US008525682B2

(12) United States Patent
Dixon et al.

(10) Patent No.: US 8,525,682 B2
(45) Date of Patent: *Sep. 3, 2013

(54) HOSPITAL BED HAVING ALERT LIGHT

(75) Inventors: Steven A. Dixon, Cincinnati, OH (US); Douglas J. Menkedick, Guilford, IN (US); William L. Jacques, II, Mount Pleasant, SC (US); James W. Jones, Gainesville, FL (US); James K. Findlay, Fishers, IN (US); Jack Wilker, Jr., Dillsboro, IN (US); Eugene E. Osborne, Hebron, KY (US); Carl W. Riley, Milan, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/563,873

(22) Filed: Aug. 1, 2012

(65) Prior Publication Data

US 2012/0291200 A1 Nov. 22, 2012

Related U.S. Application Data

(60) Continuation of application No. 13/327,999, filed on Dec. 16, 2011, now Pat. No. 8,400,311, and a continuation of application No. 13/154,553, filed on Jun. 7, 2011, now Pat. No. 8,258,963, and a continuation of application No. 12/912,330, filed on Oct. 26, 2010, now Pat. No. 7,978,084, and a continuation of application No. 11/851,535, filed on Sep. 7, 2007, now Pat. No. 7,834,768, and a continuation of application No. 11/774,744, filed on Jul. 9, 2007, now Pat. No. 7,986,242, and a continuation of application No. 11/088,468, filed on Mar. 24, 2005, now abandoned, and a continuation of (Continued)

(51) Int. Cl.
*G08B 23/00* (2006.01)
(52) U.S. Cl.
USPC ............... 340/573.4; 340/573.1; 340/665; 340/666; 340/667; 340/539.12; 340/286.07
(58) Field of Classification Search
USPC ............ 340/573.4, 573.1, 539.12, 665, 666, 340/667, 686.1, 286.07; 128/900, 905; 188/9, 188/10, 20, 21; 600/300, 301
See application file for complete search history.

(56) References Cited

U.S. PATENT DOCUMENTS

| 1,078,077 | A | 11/1913 | Arnold |
| 2,527,111 | A | 10/1950 | Widrich et al. |

(Continued)

FOREIGN PATENT DOCUMENTS

| DE | 3313843 | 10/1984 |
| DE | 3716917 | 12/1988 |

(Continued)

OTHER PUBLICATIONS

Advance Series Bed Services Manual (man026re) "4.37 Head Screw Assembly Chapter 4: Removal, Replacement, and Adjustment Procedures", Sep. 1998, pp. 89-106.

(Continued)

*Primary Examiner* — Hung T. Nguyen
(74) *Attorney, Agent, or Firm* — Barnes & Thornburg LLP

(57) ABSTRACT

A bed includes a frame, a controller coupled to the frame, and a patient position detection system coupled to the frame and coupled to the controller. The patient position detection system has multiple modes of operation of varying sensitivities for determining whether a person supported on the frame has moved by a sufficient amount to activate an alarm. The frame includes a plurality of barriers. An alert light is coupled to one of the barriers.

19 Claims, 14 Drawing Sheets

Related U.S. Application Data application No. 10/940,480, filed on Sep. 14, 2004, now abandoned, and a continuation of application No. 10/038,986, filed on Nov. 19, 2001, now Pat. No. 6,791,460, and a continuation of application No. 09/737,111, filed on Dec. 14, 2000, now Pat. No. 6,320,510, and a division of application No. 09/264,174, filed on Mar. 5, 1999, now Pat. No. 6,208,250.

(56) References Cited

U.S. PATENT DOCUMENTS

| | | |
|---|---|---|
| 3,325,799 A | 6/1967 | Farris |
| 3,504,540 A | 4/1970 | Pradko et al. |
| 3,618,592 A | 11/1971 | Stewart |
| 3,697,846 A | 10/1972 | Mueleer |
| 3,760,794 A | 9/1973 | Basham |
| 3,802,417 A | 4/1974 | Lang |
| 3,826,145 A | 7/1974 | McFarland |
| 3,836,900 A | 9/1974 | Mansfield |
| 3,890,958 A | 6/1975 | Fister et al. |
| 3,898,981 A | 8/1975 | Basham |
| 3,926,177 A | 12/1975 | Hardway, Jr. et al. |
| RE28,754 E | 3/1976 | Cook et al. |
| 3,961,201 A | 6/1976 | Rosenthal |
| 3,991,414 A | 11/1976 | Moran |
| 3,991,746 A | 11/1976 | Hanna |
| 4,020,482 A | 4/1977 | Feldl |
| 4,038,709 A | 8/1977 | Kerwit |
| 4,051,522 A | 9/1977 | Healy et al. |
| 4,097,939 A | 7/1978 | Peck et al. |
| 4,172,216 A | 10/1979 | O'Shea |
| 4,175,263 A | 11/1979 | Triplett et al. |
| 4,179,692 A | 12/1979 | Vance |
| 4,183,015 A | 1/1980 | Drew et al. |
| 4,195,287 A | 3/1980 | McCoy et al. |
| 4,196,425 A | 4/1980 | Williams, Jr. et al. |
| 4,197,854 A | 4/1980 | Kasa |
| 4,228,426 A | 10/1980 | Roberts |
| 4,242,672 A | 12/1980 | Gault |
| 4,245,651 A | 1/1981 | Frost |
| 4,264,904 A | 4/1981 | McCoy et al. |
| 4,275,385 A | 6/1981 | White |
| 4,295,133 A | 10/1981 | Vance |
| 4,320,766 A | 3/1982 | Alihanka et al. |
| 4,426,884 A | 1/1984 | Polchaninoff |
| 4,435,862 A | 3/1984 | King et al. |
| 4,484,043 A | 11/1984 | Musick et al. |
| 4,539,560 A | 9/1985 | Fleck et al. |
| 4,561,440 A | 12/1985 | Kubo et al. |
| 4,565,910 A | 1/1986 | Musick et al. |
| 4,592,104 A | 6/1986 | Foster et al. |
| 4,601,356 A | 7/1986 | Muccillo, Jr. |
| 4,633,237 A | 12/1986 | Tucknott et al. |
| 4,638,307 A | 1/1987 | Swartout |
| 4,669,136 A | 6/1987 | Waters et al. |
| 4,680,790 A | 7/1987 | Packard et al. |
| 4,700,180 A | 10/1987 | Vance |
| 4,751,754 A | 6/1988 | Bailey et al. |
| 4,793,428 A | 12/1988 | Swersey |
| 4,803,744 A | 2/1989 | Peck et al. |
| 4,907,845 A | 3/1990 | Wood |
| 4,921,295 A | 5/1990 | Stollenwerk |
| 4,926,951 A | 5/1990 | Carruth et al. |
| 4,934,468 A * | 6/1990 | Koerber et al. ............... 177/144 |
| 4,953,243 A | 9/1990 | Birkmann |
| 4,953,244 A | 9/1990 | Koerber, Sr. et al. |
| 4,974,692 A | 12/1990 | Carruth et al. |
| 4,998,939 A | 3/1991 | Potthast et al. |
| 5,010,774 A | 4/1991 | Kikuo et al. |
| 5,023,967 A | 6/1991 | Ferrand |
| 5,060,174 A | 10/1991 | Gross |
| 5,115,223 A | 5/1992 | Moody |
| 5,117,521 A | 6/1992 | Foster et al. |
| 5,137,033 A | 8/1992 | Norton |
| 5,138,729 A | 8/1992 | Ferrand |
| 5,144,284 A | 9/1992 | Hammett |
| 5,161,274 A | 11/1992 | Hayes et al. |
| 5,170,364 A | 12/1992 | Gross et al. |
| 5,184,112 A | 2/1993 | Gusakov |
| 5,195,198 A | 3/1993 | Travis |
| 5,239,300 A | 8/1993 | Berger et al. |
| 5,253,656 A | 10/1993 | Rincoe et al. |
| 5,269,388 A | 12/1993 | Reichow et al. |
| 5,276,432 A | 1/1994 | Travis |
| 5,279,010 A * | 1/1994 | Ferrand et al. ............... 5/600 |
| 5,317,769 A | 6/1994 | Weismiller et al. |
| 5,353,012 A | 10/1994 | Barham et al. |
| 5,377,372 A | 1/1995 | Rudolf et al. |
| 5,393,935 A | 2/1995 | Hasty et al. |
| 5,410,297 A | 4/1995 | Joseph et al. |
| 5,444,880 A | 8/1995 | Weismiller et al. |
| 5,450,639 A | 9/1995 | Weismiller et al. |
| 5,502,853 A | 4/1996 | Singleton et al. |
| 5,542,138 A | 8/1996 | Williams et al. |
| 5,561,412 A | 10/1996 | Novak et al. |
| 5,611,096 A * | 3/1997 | Bartlett et al. ............... 5/617 |
| 5,633,627 A | 5/1997 | Newham |
| 5,640,145 A | 6/1997 | Newham |
| 5,654,694 A | 8/1997 | Newham |
| 5,689,839 A | 11/1997 | Laganiere et al. |
| 5,699,038 A | 12/1997 | Ulrich et al. |
| 5,713,856 A | 2/1998 | Eggers et al. |
| 5,715,548 A | 2/1998 | Weismiller et al. |
| 5,771,511 A * | 6/1998 | Kummer et al. ............... 5/600 |
| 5,774,914 A | 7/1998 | Johnson et al. |
| 5,806,111 A | 9/1998 | Heimbrock et al. |
| 5,808,552 A * | 9/1998 | Wiley et al. ............... 340/573.4 |
| 5,830,149 A | 11/1998 | Oka et al. |
| 5,838,223 A | 11/1998 | Gallant et al. |
| 5,859,390 A * | 1/1999 | Stafford et al. ............... 177/144 |
| 5,878,452 A * | 3/1999 | Brooke et al. ............... 5/428 |
| 5,906,016 A | 5/1999 | Ferrand et al. |
| 6,000,076 A | 12/1999 | Webster et al. |
| 6,008,598 A | 12/1999 | Luff et al. |
| 6,014,346 A * | 1/2000 | Malone ............... 368/10 |
| 6,014,784 A | 1/2000 | Taylor et al. |
| 6,021,533 A | 2/2000 | Ellis et al. |
| 6,049,281 A | 4/2000 | Osterweil |
| 6,057,689 A | 5/2000 | Saadat |
| 6,067,019 A * | 5/2000 | Scott ............... 340/573.4 |
| 6,078,261 A * | 6/2000 | Davsko ............... 340/573.4 |
| 6,147,592 A | 11/2000 | Ulrich et al. |
| 6,163,903 A * | 12/2000 | Weismiller et al. ............... 5/610 |
| 6,166,644 A | 12/2000 | Stroda |
| 6,188,407 B1 | 2/2001 | Smith et al. |
| 6,199,508 B1 | 3/2001 | Miale et al. |
| 6,208,250 B1 | 3/2001 | Dixon et al. |
| 6,226,819 B1 | 5/2001 | Ogawa et al. |
| 6,240,579 B1 | 6/2001 | Hanson et al. |
| 6,252,512 B1 | 6/2001 | Riley |
| 6,279,183 B1 | 8/2001 | Kummer et al. |
| 6,286,166 B1 | 9/2001 | Henley et al. |
| 6,320,510 B2 | 11/2001 | Menkedick et al. |
| 6,321,878 B1 | 11/2001 | Mobley et al. |
| 6,336,235 B1 | 1/2002 | Ruehl |
| 6,351,861 B1 | 3/2002 | Shows et al. |
| 6,362,725 B1 | 3/2002 | Ulrich et al. |
| 6,378,152 B1 | 4/2002 | Washburn et al. |
| 6,396,224 B1 | 5/2002 | Luff et al. |
| 6,430,766 B1 | 8/2002 | Henley et al. |
| 6,473,921 B2 | 11/2002 | Brooke et al. |
| 6,481,688 B1 | 11/2002 | Welling et al. |
| 6,493,568 B1 | 12/2002 | Bell et al. |
| 6,611,979 B2 | 9/2003 | Welling et al. |
| 6,658,680 B2 | 12/2003 | Osborne et al. |
| RE38,419 E | 2/2004 | Auer et al. |
| 6,691,346 B2 | 2/2004 | Osborne et al. |
| 6,761,344 B2 | 7/2004 | Welling et al. |
| 6,781,517 B2 | 8/2004 | Moster et al. |
| 6,791,460 B2 | 9/2004 | Dixon et al. |
| 6,819,254 B2 | 11/2004 | Riley |
| 6,876,303 B2 | 4/2005 | Reeder et al. |
| 6,880,189 B2 | 4/2005 | Welling et al. |

| | | | |
|---|---|---|---|
| 6,892,405 B1 | 5/2005 | Dimitriu et al. |
| 6,897,780 B2 | 5/2005 | Ulrich et al. |
| 6,957,461 B2 | 10/2005 | Osborne et al. |
| 6,978,500 B2 | 12/2005 | Osborne et al. |
| 7,010,369 B2 | 3/2006 | Borders et al. |
| 7,017,208 B2 | 3/2006 | Weismiller et al. |
| 7,155,317 B1 | 12/2006 | Tran |
| 7,171,708 B2 | 2/2007 | Osborne et al. |
| 7,237,287 B2 | 7/2007 | Weismiller et al. |
| 7,242,308 B2 | 7/2007 | Ulrich et al. |
| 7,253,366 B2 | 8/2007 | Bhai |
| 7,296,312 B2 | 11/2007 | Menkedick et al. |
| 7,315,535 B2 | 1/2008 | Schuman |
| 7,319,386 B2 | 1/2008 | Collins, Jr. et al. |
| 7,330,127 B2 | 2/2008 | Price et al. |
| 7,437,787 B2 | 10/2008 | Bhai |
| 7,443,302 B2 | 10/2008 | Reeder et al. |
| 7,454,805 B2 | 11/2008 | Osborne et al. |
| 7,480,951 B2 | 1/2009 | Weismiller et al. |
| 7,506,390 B2 | 3/2009 | Dixon et al. |
| 7,515,059 B2 | 4/2009 | Price et al. |
| 7,520,006 B2 | 4/2009 | Menkedick et al. |
| 7,533,429 B2 | 5/2009 | Menkedick et al. |
| 7,538,659 B2 | 5/2009 | Ulrich et al. |
| 7,557,718 B2 | 7/2009 | Petrosenko et al. |
| 7,568,246 B2 | 8/2009 | Weismiller et al. |
| 7,610,637 B2 | 11/2009 | Menkedick et al. |
| 7,657,956 B2 | 2/2010 | Stacy et al. |
| 7,669,263 B2 | 3/2010 | Menkedick et al. |
| 7,676,866 B2 | 3/2010 | Toms et al. |
| 7,679,520 B2 | 3/2010 | Zerhusen et al. |
| 7,703,158 B2 | 4/2010 | Wilker, Jr. et al. |
| 7,746,218 B2 | 6/2010 | Collins, Jr. et al. |
| 7,834,768 B2 | 11/2010 | Dixon et al. |
| 7,868,740 B2 | 1/2011 | McNeely et al. |
| 7,978,084 B2 | 7/2011 | Dixon et al. |
| 7,986,242 B2 | 7/2011 | Dixon et al. |
| 2001/0011393 A1 | 8/2001 | Brooke et al. |
| 2001/0032362 A1 | 10/2001 | Welling et al. |
| 2002/0151990 A1 | 10/2002 | Ulrich et al. |
| 2005/0035871 A1 | 2/2005 | Dixon et al. |
| 2005/0166324 A1 | 8/2005 | Dixon et al. |
| 2005/0219059 A1 | 10/2005 | Ulrich et al. |
| 2007/0163045 A1 | 7/2007 | Becker et al. |
| 2007/0296600 A1 | 12/2007 | Dixon et al. |
| 2008/0010747 A1 | 1/2008 | Dixon et al. |
| 2008/0169931 A1 | 7/2008 | Gentry et al. |
| 2008/0205311 A1 | 8/2008 | Perkins et al. |
| 2009/0188731 A1 | 7/2009 | Zerhusen et al. |
| 2009/0302782 A1 | 12/2009 | Smith |
| 2009/0313758 A1 | 12/2009 | Menkedick et al. |
| 2010/0052917 A1 | 3/2010 | Sullivan et al. |
| 2011/0037597 A1 | 2/2011 | Dixon et al. |

FOREIGN PATENT DOCUMENTS

| | | |
|---|---|---|
| EP | 0 860 803 | 8/1998 |
| JP | 02-141441 | 5/1990 |
| JP | 2-156950 | 6/1990 |
| JP | 03-047860 | 2/1991 |
| JP | 7107195 | 4/1995 |
| JP | 11290395 | 4/1999 |
| JP | 11299837 | 11/1999 |
| JP | 2004-49706 | 2/2004 |
| JP | 2005-168913 | 6/2005 |
| WO | WO 97/20534 | 6/1997 |
| WO | WO 0175834 | 10/2001 |
| WO | WO 0185085 | 11/2001 |
| WO | PCT/FR2008/051949 | 10/2008 |

OTHER PUBLICATIONS

Advance Series Bed Services Manual (man026re) "Head Drive Unit Assembly—P/N 43353, 6200401 and 6200402; Chapter 5: Parts List", Sep. 1998, pp. 150-160.

SideCom.RTM. Communication System Design and Application Manual "from Hill-Rom:", Jul. 2002, 52 pages.

U.S. Appl. No. 12/912,320, filed Oct. 26, 2010, 36 pages.

U.S. Appl. No. 12/847,160, filed Jul. 30, 2010, 28 pages.

Prior Art emme3 Bed Brochure, purported by Defendants to have been published circa Mar. 1996 ("emme3 Bed Brochure Italian").

Prior Art emme3 Bed Brochure, purported by Defendants to have been published circa May 1997 ("emme3 Bed Brochure English").

Prior Art emme3 Instructions for Use, purported by Defendants to have been published circa Mar. 1998 (emme3 Instructions).

Complaint (filed Jun. 17, 2010 by Plaintiffs, Hill-Rom, Inc. Hill-Rom Services and Hill-Rom Company).

Answer and Counterclaims of Defendants Huntleigh Healthcare LLC and Huntleigh Healthcare, Inc. to the Complaint of Hill-Rom, Inc., Hil-Rom Services, Inc., and Hill-Rom Company, Inc. (filed Aug. 5, 2010 by Defendants Huntleigh Healthcare LLC and Huntleigh Healthcare, Inc.).

Reply to Counterclaims (filed Aug. 16, 2010 by Plaintiffs, Hill-Rom, Inc. Hill-Rom Services and Hill-Rom Company).

Plaintiff Hill-Rom's First Set of Interrogatories to Defendant (filed Sep. 17, 2010 by Plaintiffs, Hill-Rom, Inc. Hill-Rom Services and Hill-Rom Company).

Plaintiff Hill-Rom's First Request for the Production of Documents and Things to Defendant Huntleigh (filed Sep. 17, 2010 by Plaintiffs, Hill-Rom, Inc. Hill-Rom Services and Hill-Rom Company).

Huntleigh Healthcare LLC's First Request to Hill-Rom Services, Inc. for Production of Documents and Things (filed Sep. 22, 2010 by Defendants Huntleigh Healthcare LLC and Huntleigh Healthcare, Inc.).

Huntleigh Healthcare LLC's First Request to Hill-Rom Company, Inc. for Production of Documents and Things (filed Sep. 22, 2010 by Defendants Huntleigh Healthcare LLC and Huntleigh Healthcare, Inc.).

Huntleigh Healthcare LLC's First Request to Hill-Rom, Inc. for Production of Documents and Things (filed Sep. 22, 2010 by Defendants Huntleigh Healthcare LLC and Huntleigh Healthcare, Inc.).

Defendant Hunteligh Healthcare LLC's First Set of Interrogatories (Nos. 1-11) to Plaintiff Hill-Rom Company, Inc. (filed Sep. 22, 2010 by Defendants Huntleigh Healthcare LLC and Huntleigh Healthcare, Inc.).

Defendant Hungleigh Healthcare LLC's First Set of Interrogatories (Nos. 1-11) to Plaintiff Hill-Rom Services, Inc. (filed Sep. 22, 2010 by Defendants Huntleigh Healthcare LLC and Huntleigh Healthcare, Inc.).

Defenant Huntleigh Healthcare LLC's First Set of Interrogatories (Nos. 1-11) to Plaintiff Hill-Rom, Inc. (filed Sep. 22, 2010 by Defendants Huntleigh Healthcare LLC and Huntleigh Healthcare, Inc.).

Hill-Rom's Initial Disclosures (filed Sep. 30, 2010 by Plaintiffs, Hill-Rom, Inc. Hill-Rom Services and Hill-Rom Company).

Initial Disclosures for Defendants Huntleigh Healthcare LLC, and Huntleigh Healthcare, Inc. (filed Sep. 30, 2010 by Defendants Huntleigh Healthcare LLC and Huntleigh Healthcare, Inc.).

Case Management Plan Order (filed Nov. 5, 2010).

Plaintiffs' Preliminary Infringement Contentions (filed Nov. 5, 2010 by Plaintiffs, Hill-Rom, Inc. Hill-Rom Services and Hill-Rom Company).

Responses and Objections of Defendants Huntleigh Healthcare LLC and Huntleigh Healthcare Inc. to Plaintiff Hil-Rom's First Set of Interrogatories (1-5) (filed Nov. 18, 2010 by Defendants Huntleigh Healthcare LLC and Huntleigh Healthcare, Inc.).

Responses and Objections of Defendants Huntleigh Healthcare LLC and Huntleigh Healthcare Inc to Plaintiff Hill-Rom's First Request for Documents and Things (filed Nov. 18, 2010 by Defendants Huntleigh Healthcare LLC and Huntleigh Healthcare, Inc.).

Plaintiffs Hill-Rom, Inc.'s Hill-Rom Services, Inc.'s and Hill-Rom Company, Inc.'s Consolidated Answers and Objections to Defendant Huntleigh Healthcare LLC's First Set of Interrogatories (Nos. 1-11) (filed Nov. 22, 2010 by Plaintiffs, Hill-Rom, Inc. Hill-Rom Services and Hill-Rom Company).

Plainitffs Hill-Rom, Inc.'s, Hill-Rom Services, Inc.'s and Hill-Rom Company, Inc.'s Consolidated Responses and Objections to Defendant Hunteligh Healthcare LLC's First Request for Production of Documents and Things (filed Nov. 22, 2010 by Plaintiffs, Hill-Rom, Inc. Hill-Rom Services and Hill-Rom Company).

Defendants' Preliminary Invalidity Contentions (filed Dec. 22, 2010 by Defendants Huntleigh Healthcare LLC and Huntleigh Healthcare, Inc.)—Exhibits A-H.

Centra from Hill-Rom, Hill-Rom 1992.
In Services Manual Centra Bed from Hill-Rom, Hill-Rom 1996.
The Advance 2000 Bed from Hill-Rom, Hill-Rom 1993.
Adel 500XL Childbearing Bed, Stryker Patient Care, May 1995.
Stryker Adel 2100EC Childbearing Bed, Stryker Patient care, Jan. 1994.

Advantage Stretcher Stryker Patient Handling, May 1994.
Hausted Gemini Series, Hausted, Inc., Oct. 1993.
Stryker Adel 500XL Childbearing Bed Service Manual, Adel Medical Ltd. 1986.

* cited by examiner

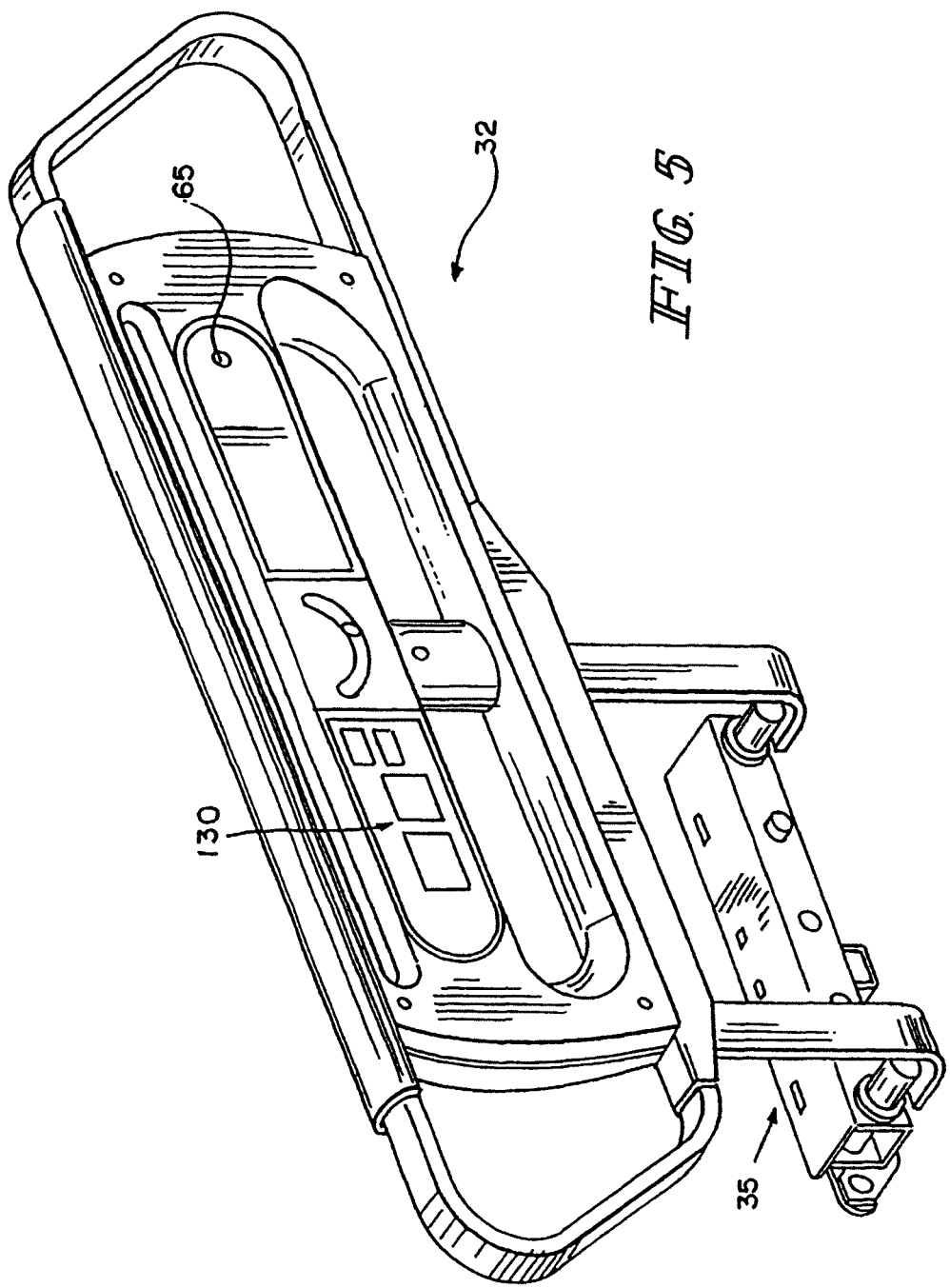

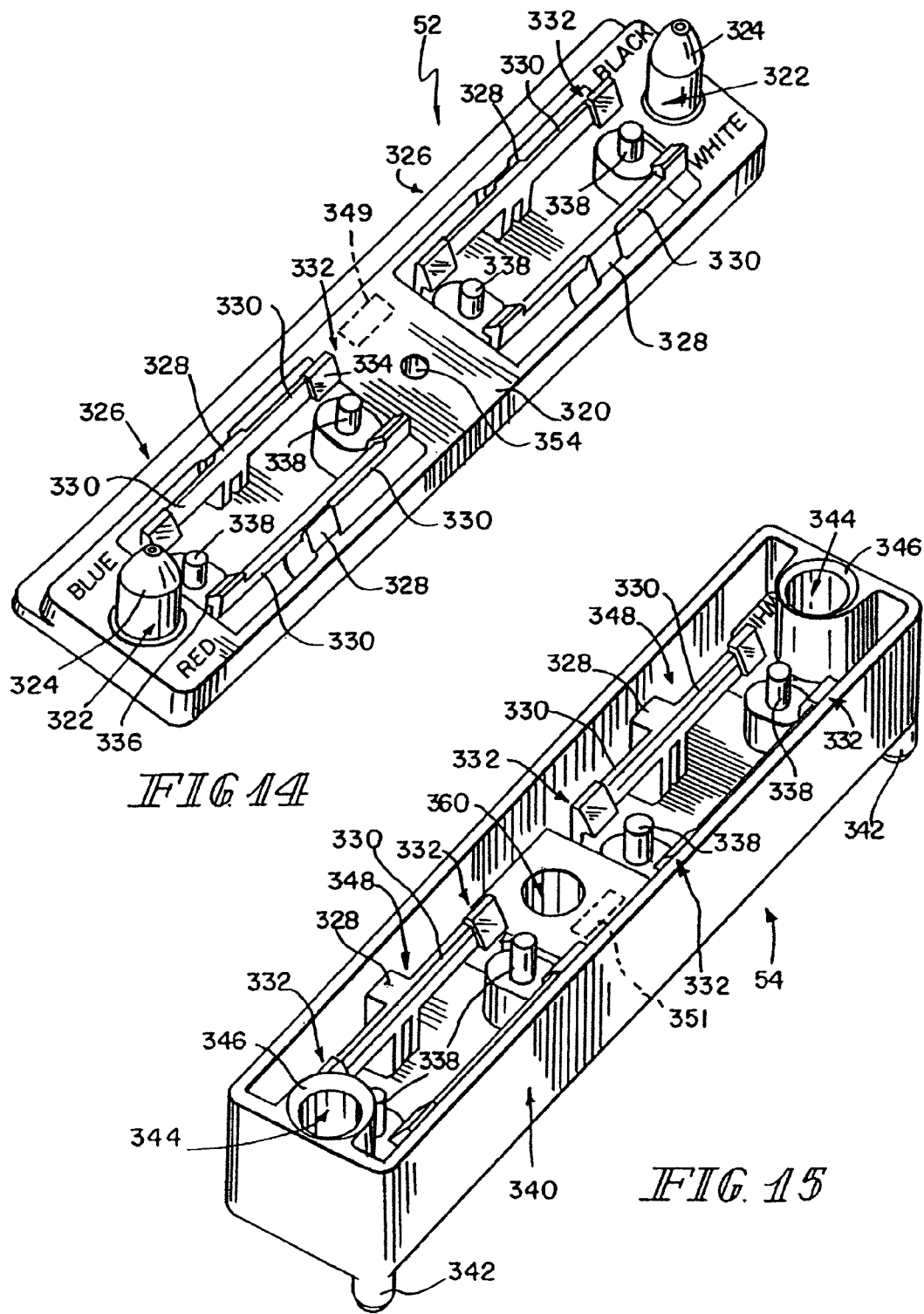

HOSPITAL BED HAVING ALERT LIGHT

RELATED APPLICATIONS

This application is a continuation of U.S. application Ser. No. 13/327,999, filed Dec. 16, 2011, now U.S. Pat. No. 8,400,311, which is a continuation of U.S. patent application Ser. No. 13/154,553, filed Jun. 7, 2011, now U.S. Pat. No. 8,258,963, which is a continuation of U.S. patent application Ser. No. 12/912,330, filed Oct. 26, 2010, now U.S. Pat. No. 7,978,084, which is a continuation of U.S. patent application Ser. No. 11/851,535, filed Sep. 7, 2007, now U.S. Pat. No. 7,834,768, which is a continuation of U.S. patent application Ser. No. 11/774,744, filed Jul. 9, 2007, now U.S. Pat. No. 7,986,242, which is a continuation of U.S. patent application Ser. No. 11/088,468, filed Mar. 24, 2005, now abandoned, which is a continuation of U.S. patent application Ser. No. 10/940,480, filed Sep. 14, 2004, now abandoned, which is a continuation of U.S. patent application Ser. No. 10/038,986, filed Nov. 19, 2001, now U.S. Pat. No. 6,791,460, which is a continuation of U.S. patent application Ser. No. 09/737,111, filed Dec. 14, 2000, now U.S. Pat. No. 6,320,510, which is a divisional of U.S. patent application Ser. No. 09/264,174, filed Mar. 5, 1999, now U.S. Pat. No. 6,208,250, the disclosures of all of which are hereby incorporated herein by reference in their entirety.

BACKGROUND SUMMARY OF THE INVENTION

The present invention relates to a patient position detection apparatus for a bed. More particularly, the present invention relates to a bed exit and patient position detection apparatus which has multiple modes of operation for providing information to a caregiver regarding a location of a patient on a support deck of the bed and for providing an indication when the patient has exited the bed.

When a patient is required to stay in a hospital bed at a hospital or other patient care facility, it is desirable for a caregiver to be able to monitor the presence, absence, and location of the patient on the bed support surface and to monitor the patient's activity level. Caregivers within a hospital or other patient care facilities are continuously responsible for more and more activities. One of these activities is monitoring patients who need to be restricted to the bed or patients that are at a risk of falling or aggravating injuries if they exit the bed. Patients having certain patient profiles, such as confusion, weakness, or disorientation, are more likely to be injured or reinjured if they exit the bed. Patients with certain types of medical conditions therefore require monitoring of both their presence on the bed and their or location on the support surface. In this instance, the present invention provides an alarm when the patient moves out of the predetermined position on the bed, prior to exiting the bed.

Some patients are allowed by doctor's orders to move about freely on the bed in order to access the bed controls, a phone, or other items or to reposition themselves for comfort. In this situation, an alarm is only required if the patient totally exits the bed.

The present invention provides dual sensor mechanisms for detecting the location of the patient on the bed and for detecting bed exit. Therefore, the caregiver may select from various modes of operation depending upon the patient condition and profile. The apparatus of the present invention detects the presence or absence of the patient on the bed and also detects the position of the patient on the support surface. Therefore, the present invention allows proper patient monitoring to be applied at the discretion of the caregiver for the correct patient situation.

The apparatus of the present invention utilizes two different sensor technologies integrated into the support sections of the hospital bed frame and deck. A controller monitor inputs from both types of sensors and, depending upon the mode selected by the caregiver, results in an alarm or no alarm based on detected sensor conditions.

In an illustrated embodiment of the invention, a first set of sensors includes load cells mounted on a base frame of the bed to support a weigh frame. As weight is applied to the bed, such as when a patient enters the bed, the controller detects voltage changes from the load cells. A second set of sensors is located below the patient. These second sensors are illustratively pressure sensitive sensors, such as resistive sensors which are located on the support deck or within the mattress. As pressure is applied to these sensors, such as when a patient lies on the mattress, a resultant voltage corresponds to the amount of pressure applied to a particular sensor. As the patient moves about the bed, sensor resistances change accordingly, thereby providing the controller with data to analyze regarding patient positions.

Each sensor provides an input to the common controller and all of the inputs are evaluated by the controller. When certain weight distribution changes are detected, an audible or visual alarm is activated. The criteria for activating the alarm is dependent upon the particular mode of operation for the overall system. Multiple modes of operation are selected by a switch, knob, button, etc. located on the bed, and preferably on a siderail of the bed. It is understood that a control panel on a pendant or remote control input device electrically coupled to the controller may be used to select the modes.

In an out-of-bed mode, an alarm is activated only when a patient completely exits the bed. In an exiting mode, an alarm is activated when a patient is located at a pre-exit position near the sides or ends of the support surface of the bed. Finally, in a position mode, an alarm is activated when a patient moves away from a head support surface on the deck located beneath the patient's head and back, such as when the patient has rolled against a siderail of the bed or has sat up in bed. Therefore, position mode provides an alarm earlier than exiting mode.

In the exiting mode and position mode, an alarm will also be activated if the patient exits the bed. In other words, in exiting mode and position mode, the out-of-bed detector is also used.

The alarm tones of the apparatus may be selected from a number of various tone options. Different sounds or visual indicators may be provided for each of the modes, if desired. In one illustrated embodiment, the patient positioning system is configured to deactivate the alarm if the patient gets back into bed or returns to the correct position on the bed. The apparatus also includes a button, switch, etc. located on the bed which will send a signal to reset or clear the "nurse call" alarm which is activated at a remote nurse station when a patient alarm is generated by the apparatus. This button allows the nurse to clear the remote bed exit/patient position alarm while at the bed after responding to the alarm. Currently, nurses have to clear the bed exit/patient position alarm by returning to the nurse call station or by deactivating the alarm somewhere else in the hospital, other than at the bed. Another illustrated embodiment of the invention is configured to turn on the room lights when an alarm is activated.

According to an illustrated embodiment of the present invention, an apparatus is provided for detecting a position of a body on a support surface of a bed. The apparatus includes at least one first sensor coupled to the bed and at least one second sensor located adjacent the support surface. The at least one first sensor has an output signal which is variable in response to changes in a weight applied to the support surface. The at least one second sensor has an output signal which is variable in response to changes in the position of the body on the support surface. The apparatus also includes a controller having inputs configured to receive the output signals from the first and second sensors. The controller is configured to monitor the output signals, to provide an indication of changes in the position of the body relative to the support surface, and to provide an indication if the body exits the support surface.

In the illustrated embodiment, the first and second sensors are different types of sensors. The at least one first sensor is illustratively a load cell or other suitable sensor. The at least one second sensor is illustratively a resistive pressure sensor, a capacitance sensor, a piezoelectric sensor, or other suitable sensor.

The bed illustratively includes a base frame and a weigh frame. The weigh frame is configured to support the support surface of the bed. The at least one first sensor includes a plurality of load cells configured to couple the weigh frame to the base frame. Each of the plurality of load cells is electrically coupled to the controller.

The support surface of the bed illustratively includes a deck and a mattress located on the deck. In one embodiment, the at least one second sensor is coupled to the mattress. The at least one second sensor is either coupled to a top or bottom surface of the mattress or located within an interior region of the mattress.

In another illustrated embodiment, the at least one second sensor is coupled to the deck. The deck illustratively includes a head deck section, a seat deck section, a thigh deck section, and a leg deck section. The second sensors illustratively include at least one head sensor coupled to the head deck section, at least one seat sensor coupled to the seat deck section, and at least one thigh sensor coupled to the thigh deck section.

In the illustrated embodiment, the head sensor is an elongated strip which extends in a direction parallel to a longitudinal axis of the deck. The head sensor is located at a center portion of the head deck section. Two elongated thigh sensors are illustratively coupled to the thigh deck section. The elongated thigh sensors illustratively extend in a direction parallel to the longitudinal axis of the deck. The seat sensor is an elongated strip which is configured to extend in a direction transverse to the longitudinal axis of the deck. The second sensors may further include at least one leg sensor coupled to the leg deck section.

The illustrated apparatus further includes an alarm coupled to the controller. The controller has a first mode of operation in which the alarm is activated by the controller only when the at least one first sensor detects that the body has exited the bed, a second mode of operation in which the alarm is activated by the controller when the at least one second sensor detects that the body has moved away from a central portion of the support surface, and a third mode of operation in which the alarm is activated by the controller when the at least one second sensor detects that the body has moved away from a central portion of a head section of the deck.

The illustrated apparatus further includes first, second, and third mode indicator lights located on the bed which correspond to the first, second, and third modes of operation of the controller, respectively. The controller is coupled to the first, second, and third mode indicator lights. The controller is configured to illuminate the first mode indicator light when the controller is in the first operation mode, to illuminate the first and second mode indicator lights when the controller is in the second operation mode, and to illuminate the first, second, and third mode indicator lights when the controller is in the third operation mode.

The illustrated apparatus includes a control panel coupled to the controller to permit a caregiver to select between the first and second modes of operation. The control panel is illustratively either coupled to a siderail of the bed, located on a pendant coupled to the controller, coupled to the controller by a remote control transmitter, or located elsewhere on the bed.

In an alternative embodiment of the present invention, the controller is configured to activate the alarm when the patient is out of a predetermined position on the support surface. The controller is also configured to detect when the body moves back into the predetermined position on the support surface and automatically deactivate the alarm upon detection of the body moving back into the predetermined position on the support surface.

In yet another embodiment, the controller is configured to monitor movement of the body on the support surface. The controller is configured to generate an output signal if a predetermined amount of movement of the body is not detected within a predetermined period of time.

In an illustrated embodiment, the controller includes an output coupled to a communication port to provide a nurse call alarm upon detection of the body moving out of a predetermined position on the support surface of the bed. A nurse call clear actuator is coupled to the bed. The nurse call clear actuator is configured to clear the nurse call alarm. The controller also is configured to transmit an output signal through the communication port to a remote location over a communication network.

According to another illustrated embodiment of the present invention. An apparatus is provided for detecting a position of a body on a support surface of a bed. The apparatus includes at least one sensor coupled to the bed. The at least one sensor has an output signal which is variable in response to changes to in the position of the body on the support surface. The apparatus also includes an alarm and a controller having at least one input configured to received the output signal from the at least one sensor and an output coupled to the alarm. The controller has at least two different modes of operation to monitor the position of the body on the support surface and generate an alarm signal to activate the alarm if predetermined conditions are met. The apparatus further includes a control panel coupled to the controller. The control panel includes a key button and a separate mode button to permit a caregiver to change the mode of operation of the controller. The controller is configured to permit a caregiver to adjust the mode of operation by pressing the mode button only when the key button is also pressed.

The control panel is illustratively coupled to a siderail of the bed, located on a pendant coupled to the controller, coupled to the controller by a remote control transmitter, or located elsewhere on the bed. The illustrated control panel also includes an alarm volume control button. The controller being configured to permit the caregiver to adjust the volume of the alarm using the volume control button only when the key button is also pressed. In other illustrated embodiments, the control panel includes an actuator to permit a tone of the alarm to be selected from a plurality of different tones, and the controller is configured to turn on a room light wherein the alarm signal is generated.

In the illustrated embodiment, the controller has first, second and third different modes of operation. The alarm is activated by the controller when different levels of patient movement on the support surface are detected for the first, second and third modes of operation. The apparatus also includes first, second, and third mode indicator lights located on the control panel which correspond to the first, second, and third modes of operation of the controller, respectively. The controller is coupled to the first, second, and third mode indicator lights. The controller is illustratively configured to illuminate the first mode indicator light when the controller is in the first operation mode, to illuminate the first and second mode indicator lights when the controller is in the second operation mode, and to illuminate the first, second, and third mode indicator lights when the controller is in the third operation mode.

According to yet another illustrative embodiment of the present invention, a bed includes a base, a support surface coupled to the base, a controller configured to control an entertainment device including at least one of a television, a radio, a stereo, a video player, and a computer, and an entertainment control panel coupled to the controller. The entertainment control panel includes inputs to permit an operator to control operation of the entertainment device. The apparatus also includes a lockout switch coupled to the controller. The lockout switch is configured to disable the entertainment control panel when the lockout switch is actuated.

In the illustrated embodiment, an indicator light is coupled to the controller. The indicator light is illuminated when the lockout switch is actuated. The indicator light is illustratively coupled to a siderail of the bed spaced apart from the lockout switch. The lockout switch is illustratively coupled to a footboard of the bed. A cover is coupled to the footboard. The lockout switch being concealed beneath the cover.

According to still another embodiment of the present invention, a bed includes a base, a support surface coupled to the base, a controller configured to control a plurality of functions including at least one of a night light, a back light, a head articulation actuator, a knee articulation actuator, a hi/lo actuator, and an entertainment device, and a control panel coupled to the controller. The control panel includes a plurality of inputs to permit an operator to control the plurality of functions. The apparatus also includes a plurality of lockout switches coupled to the controller and an indicator located on the bed spaced apart from the plurality of lockout switches. The controller is configured to disable operation of selected functions by the control panel upon actuation of corresponding lockout switches. The indicator is configured to provide an indication when at least one of the lockout switches is actuated to disable operation of at least one of the functions.

Illustratively, the indicator is coupled to a siderail of the bed and the plurality of lockout switches are located on a footboard of the bed. Each of the plurality of lockout switches illustratively includes a separate light located adjacent the lockout switch to indicate when the lockout switch is actuated.

According to a further embodiment of the present invention, an apparatus is provided for aligning a first electrical connector electrically coupled to a control panel located on a removable member of a bed with a second electrical connector electrically coupled to a controller on the bed. The apparatus includes a first connector alignment apparatus having a connector receiving portion configured to secure the first electrical connector to the first connector alignment apparatus, a second connector alignment apparatus having a connector receiving portion configured to secure the second electrical connector to the second connector alignment apparatus, a first fastener configured to couple the first connector alignment apparatus to the removable member of the bed, and a second fastener configured to couple the second connector alignment apparatus to a frame of the bed. One of the first and second connector alignment apparatuses includes at least one alignment post, and the other of the first and second connector alignment apparatuses includes at least one aperture configured to receive the alignment post therein as the removable member is installed on to the frame of the bed to align the first and second electrical connectors before the first and second connectors are mated.

In the illustrated embodiment, the frame of the bed includes at least one post extending away from the frame by a distance greater than a height of the second connector alignment apparatus. The removable member of the bed is formed to include an aperture configured to receive the post on the frame of the bed to provide an initial alignment between the removable member and the frame as the removable member is installed on to the frame. The first electrical connector includes at least one alignment post and the second electrical connector includes an aperture configured to receive the alignment post of the first electrical connector therein to provide further alignment between the first and second electrical connectors.

In the illustrated embodiment, the first fastener is configured to provide a rigid connection between the first connector alignment apparatus and the removable member, and the second fastener is configured provide a loose connection between the second connector alignment apparatus and the frame to permit limited movement of the second connector alignment apparatus relative to the frame. The frame of the bed is illustratively formed to include at least one aperture. The second electrical connector alignment apparatus illustratively includes at least one retention post configured to be inserted into the at least one aperture of the frame. The at least one aperture of the frame is larger than the at least one retention post to permit the limited movement of the second connector alignment apparatus relative to the frame of the bed.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying figures in which:

FIG. 5 is a perspective view of a head end siderail which includes a control panel for operating the patient position detection apparatus of the present invention;

FIG. 14 is a perspective view of a first electrical connector alignment apparatus configured to be coupled to the footboard of the bed;

FIG. 15 is a perspective view of a second electrical connector alignment apparatus configured to be coupled to the retracting frame of the bed.

DETAILED DESCRIPTION OF THE DRAWINGS

Figure 1:
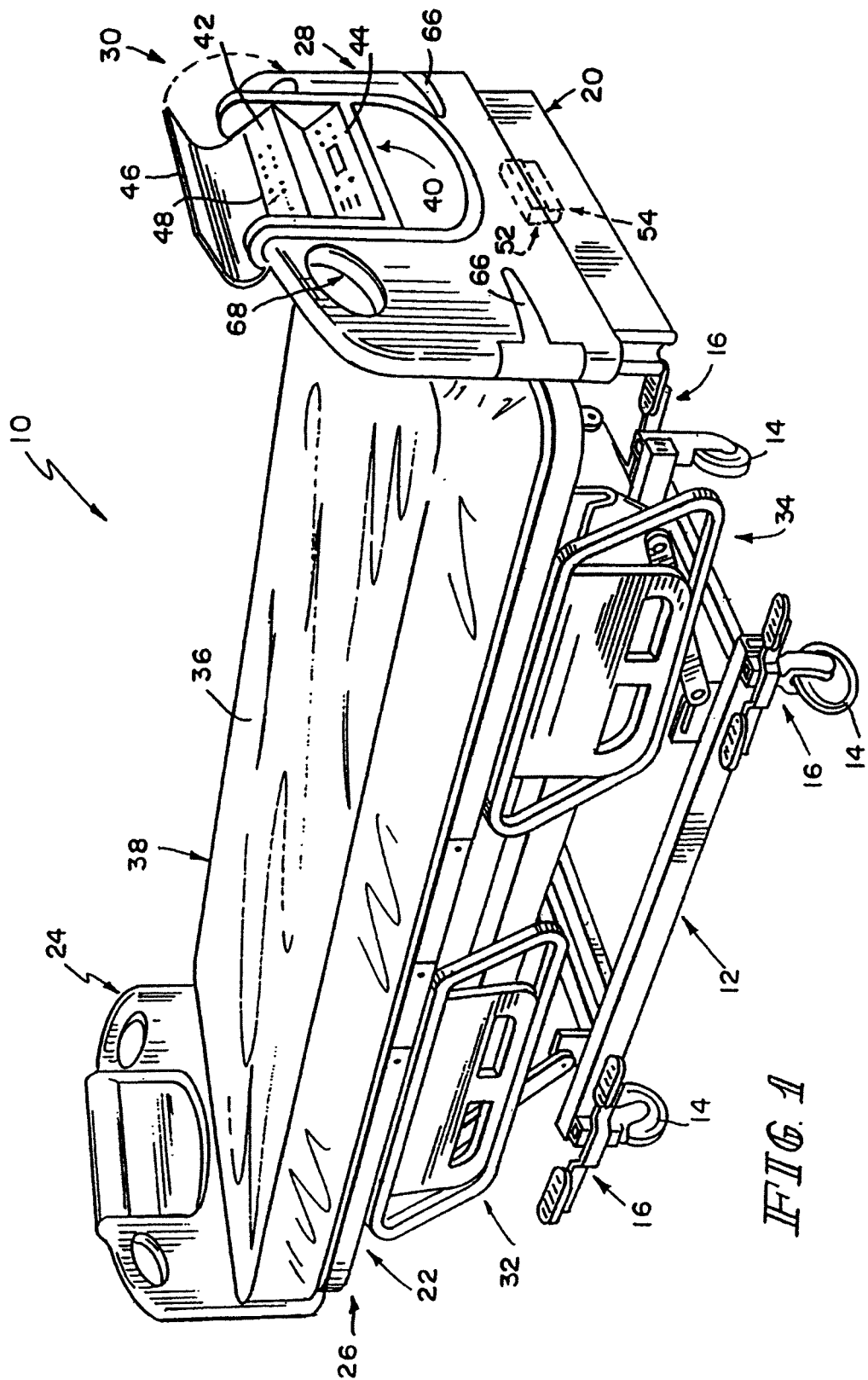
FIG. 1 is a perspective view of a hospital bed which includes a patient position detection apparatus in accordance with the present invention and which includes a footboard having an electrical connector alignment apparatus of the present invention.

Referring now to the drawings, FIG. 1 illustrates a hospital bed 10 of the present invention. The bed 10 includes a base frame 12 having a plurality of casters 14 and brake/steer control pedals 16 mounted adjacent each of the casters 14. Details of the operation of the brake/steer control mechanism are disclosed in U.S. patent application Ser. No. 09/263,039, now U.S. Pat. No. 6,321,878, which is hereby incorporated by reference.

Figure 3:
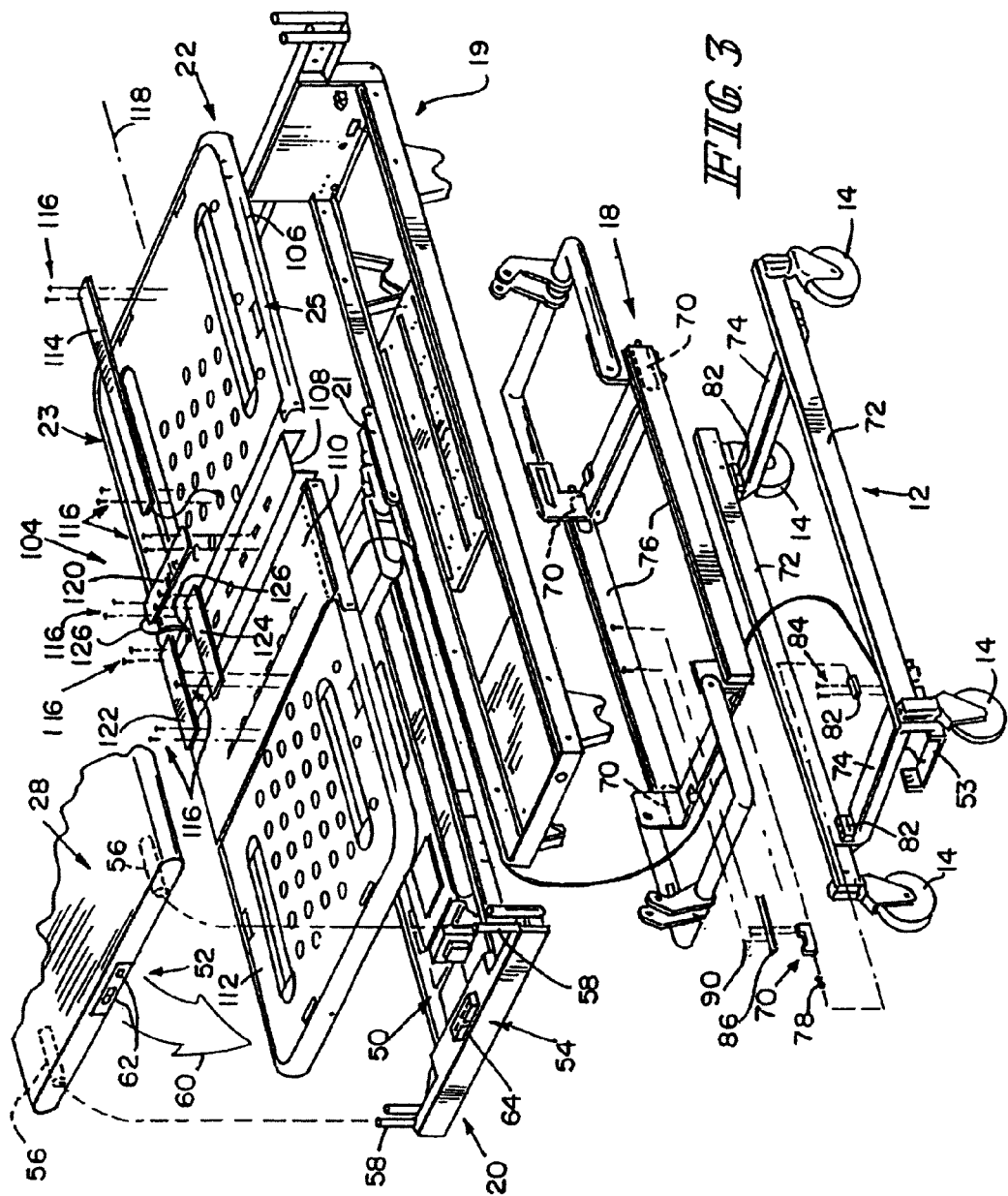
FIG. 3 is an exploded perspective view of portions of the hospital bed of FIG. 1 illustrating a base frame, a weigh frame, an intermediate frame, a retracting frame, an articulating deck, a first set of sensors for detecting the weight of a patient on the deck, and a second set of sensors located on the articulating deck for detecting the position of the patient on the deck.

As best shown in FIG. 3, the bed 10 includes a weigh frame 18 coupled to the base frame 12, an intermediate frame 19 coupled to the weigh frame 18, a retracting frame 20 coupled to the intermediate frame 19, and an articulating deck 22 coupled to the intermediate frame 19 and the retracting frame 20. Brackets 21 on opposite sides of frame 20 are configured to be coupled between the head section 106 and the thigh section 110 of deck 22 with suitable fasteners (not shown).

Referring again to FIG. 1, the bed 10 includes a headboard 24 mounted adjacent a head end 26 of the bed 10 and a footboard 28 mounted to the frame 20 adjacent a foot end 30 of bed 10. Bed 10 further includes a pair of head end siderails 32 and a pair of foot end siderails 34 mounted to the articulating deck 22 on opposite sides of the bed 10. Further details of head end siderail 32 are illustrated in FIG. 5. Siderails 32 and 34 are coupled to the articulating deck 22 in a conventional manner using a connector mechanism 35 best shown in FIG. 5. The siderails 32 and 34 are movable from a lowered position shown in FIG. 1 to an elevated position (not shown) located above a top surface 36 of mattress 38. Mattress 38 is located on articulating deck 22 for supporting a patient thereon.

The footboard 28 includes a plurality of buttons, knobs, switches or other controls 40 for controlling various functions of the bed 10. Controls 40 are located on a top inclined panel 42 and a bottom inclined panel 44 on the footboard 28. A cover 46 is pivotably coupled to the footboard 28 by a pivot connection 48 so that the cover can be pivoted downwardly to conceal at least the controls 40 located on the top inclined panel 42.

One of the controls on the footboard 28 is illustratively a lockout button 61 for entertainment functions which are controlled by patient input control panels on the bed 10. In other words, a caregiver can press button 61 to lock out entertainment functions on the bed 10. An indicator light is provided adjacent the entertainment lockout control 61 to provide an indication when the entertainment lockout 61 is activated. When the entertainment lockout 61 is activated, the patient cannot turn on the television, radio, stereo, video player, computer or other entertainment device typically available on the bed or in the room. The entertainment lockout control 61 is illustratively located below the cover 46 on the footboard 28. It is understood, however, that the entertainment lockout may be located at other positions on the bed.

The bed 10 also includes a plurality of lockout switches 63 which are illustratively located on the footboard 28. It is understood that the lockout switches 63 may be located at any other position on the bed 10. The lockout switches 63 are coupled to the controller 50 to permit a caregiver to lock out selected functions which are normally controlled by the patient. Using patient controls that are typically located on the head end siderails 32. For example, lockout switches 63 may deactivate controls for a night light, a back light, head or knee articulation, a hi/lo mechanism, or the entertainment devices discussed above. In addition, a master lockout switch is provided to lock out the head and knee articulation and the hi/lo control mechanism controls.

Panel 42 illustratively includes an indicator light (not shown) adjacent each of the lockout switches 63 to provide an indication when a particular lockout switch 63 is pressed. In addition, the bed 10 includes a separate lockout indicator light 65 located at a location on the bed 10 spaced apart from the lockout switches 63. In the illustrated embodiment, the separate lockout indicator light 65 is located on the head end siderail 32 as shown in FIG. 5. Indicator light 65 provides the nurse with a visual indication that one of the lockout switches 63 has been pressed.

Footboard 28 also includes side bumpers 66 and apertures 68. Apertures 68 provide handles to facilitate movement of the bed 10. Illustratively, headboard 24 and footboard 28 are made from a plastic material using a blow molding process. It is understood, however, that the headboard 24 and footboard 28 may be made from other materials and from other processes, if desired.

Figure 2:
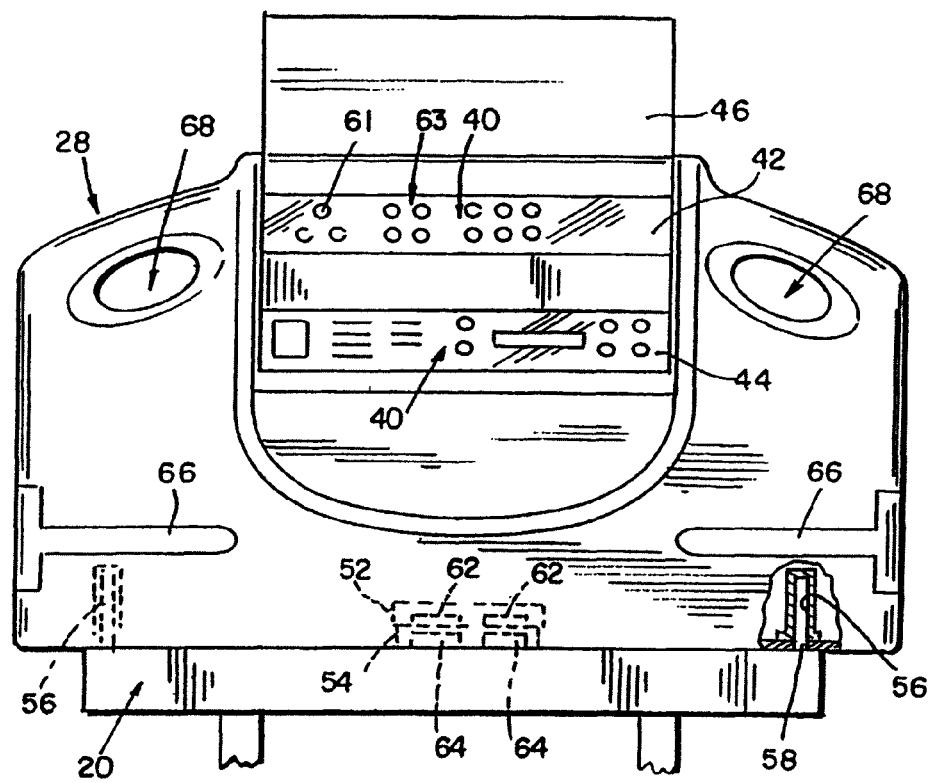
FIG. 2 is an end view of the footboard of FIG. 1 illustrating further details of the electrical connector alignment apparatus.

The controls 40 on the footboard 28 are electrically coupled to a controller 50 shown in FIG. 3. The controller 50 and other bed electronics are illustratively mounted on frame 20. A first connector alignment apparatus 52 is coupled to the footboard 28 and a second connector alignment apparatus 54 is coupled to the frame 20. As shown in FIGS. 2 and 3, footboard 28 is formed to include apertures 56 which slide over posts 58 on the frame 20 during installation of the footboard 28 onto the frame 20 in the direction of arrow 60 in FIG. 3. Posts 58 and apertures 56 therefore provide initial alignment between the footboard 28 and the frame 20. First and second connector alignment apparatuses 52 and 54 provide further alignment for male and female electrical connectors 62 and 64, respectively, as discussed in detail below with reference to FIGS. 14-16.

Figure 4:
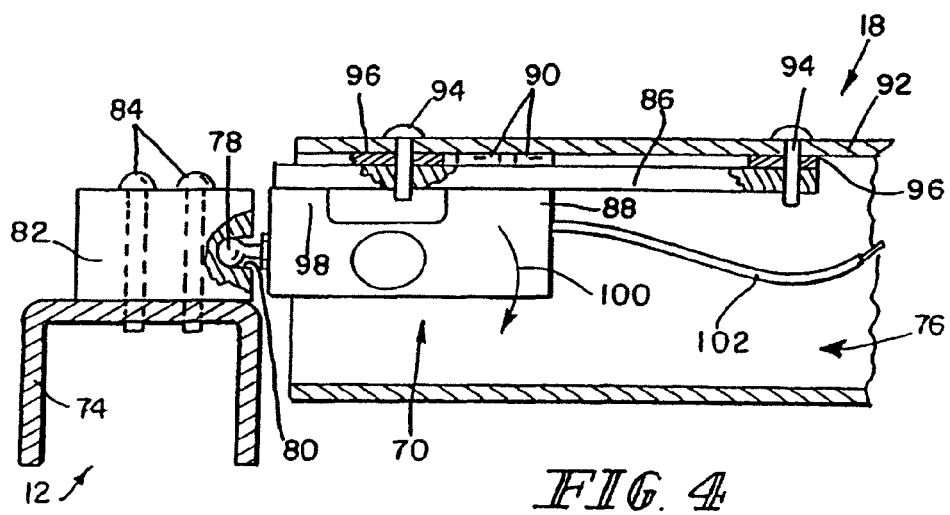
FIG. 4 is a partial sectional view illustrating a load cell configured to connect the weigh frame to the base frame.

The patient position detection apparatus of the present invention uses two different types of sensors 70, 104. A first set of sensors 70 is used to detect when a patient exits the bed 10. A second set of sensors 104 is used to determine a position of the patient on the deck 22 of the bed 10. In the illustrated embodiment, the first type of sensors include load cells 70 which are mounted at the four corners of the weigh frame 18. Details of the mounting of the load cells 70 between the base frame 12 and the weigh frame 18 are illustrated in FIGS. 3 and 4. Base frame 12 includes side frame members 72 and transverse frame members 74 extending between the side frame members 72. Weigh frame 18 includes a pair of hollow side frame members 76. Load cells 70 are well known. Load cells 70 typically include a plurality of strain gauges located within a metal block.

As best shown in FIG. 4, a mounting ball 78 is coupled to the load cell 70. Illustratively, mounting ball 78 includes a threaded stem which is screwed into threads in the load cell 70. Mounting ball 78 is located within an aperture 80 formed in a mounting block 82. Mounting blocks 82 are secured to the transverse frame members 74 by suitable fasteners 84 at the four corners of the base frame 12. A mounting bar 86 is coupled to an arm 88 of load cell 70 by fasteners 90. Mounting bar 86 is then secured to a top surface 92 of side frame member 76 of weigh frame 18 by suitable fasteners 94 and washers 96. Mounting bar 86 is not coupled to arm 98 of load cell 70. Therefore, load cell 70 may be deflected downwardly in the direction of arrow 100 when weight is applied to the weigh frame 18. Such deflection in the direction of arrow 100 changes an output voltage which provides an indication of weight change on the weigh frame. Load cells 70 are coupled to a signal conditioner 53 by wires 102. The signal conditioner 53 is then coupled to the controller 50 on the bed 10 by wires 102.

Although the specification and claims of this application refer to a controller 50, it is understood that the bed 10 will typically include several controllers which control different functions on the bed. These controllers may be located at any location on the bed and are not limited to the location illustrated in FIG. 3. The controllers 10 typically are microprocessor based controllers. Output signals from various devices may need to be conditioned prior to being coupled to the controller. For instance, analog signals may need to be converted to digital signals for processing by the microprocessor of the controller. Therefore, the word controller is used broadly to include any type of control circuitry necessary to process the output signals and produce the desired control outputs or signals.

Figure 8:
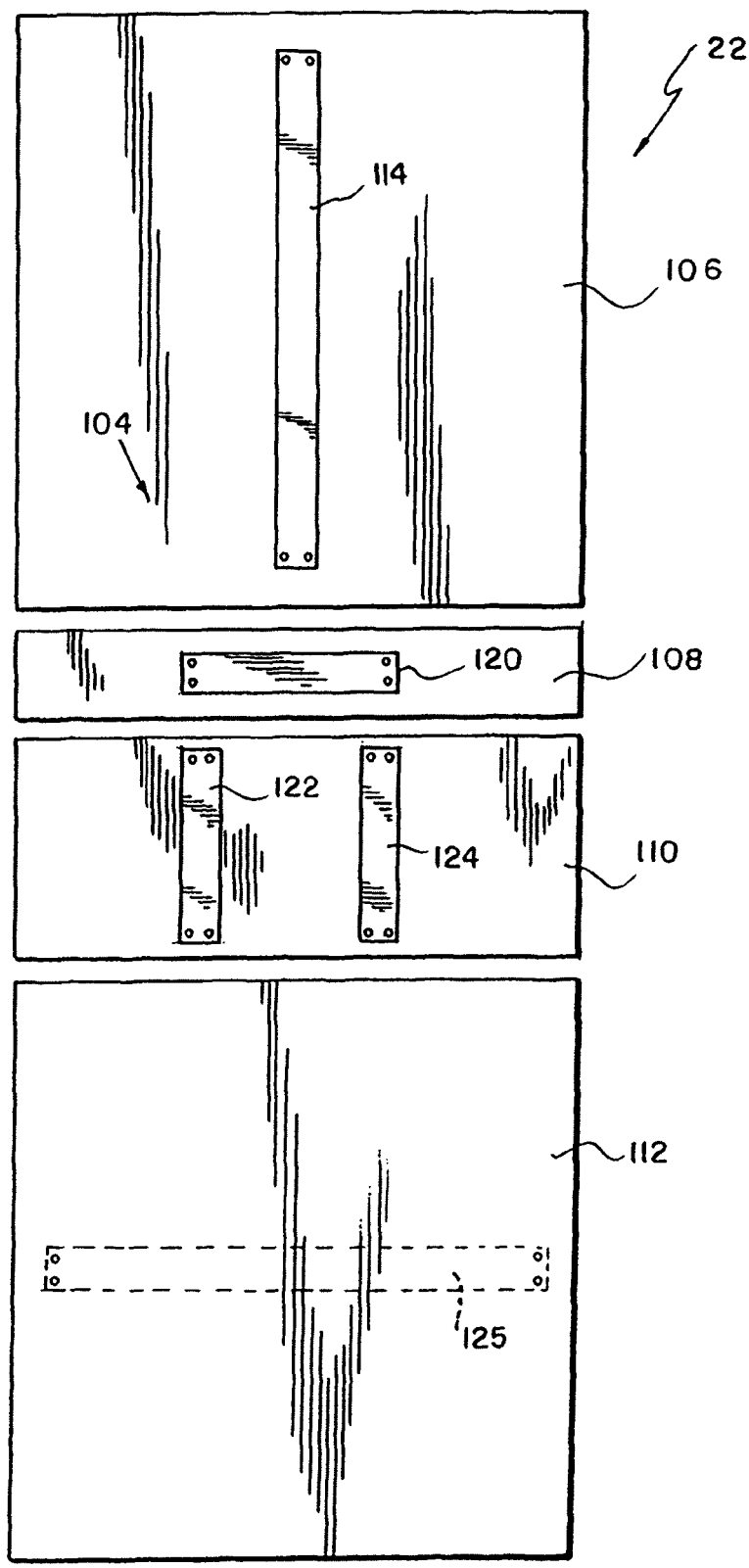
FIG. 8 is a top plan view of the articulating deck of the bed with the second set of sensors mounted on the deck.

A second set of sensors 104 is illustrated in FIGS. 3 and 8. Articulating deck 22 includes a head deck section 106, a seat deck section 108, a thigh deck section 110, and a leg deck section 112. The second set of sensors 104 includes a head section sensor 104 coupled to head deck section 106 by fasteners 116. Sensor 114 is elongated and extends along a longitudinal axis 118 of the deck 22. Seat sensor 120 is coupled to seat deck section 108 by fasteners 116. Sensor 120 extends in a direction transverse to the longitudinal axis 118. Thigh sensors 122 and 124 are coupled to thigh deck section 110 by fasteners 116. The locations of sensors 114, 120, 122, 124 are further illustrated in FIG. 8.

Illustratively, sensors 114, 120, 122, and 124 are resistive pressure sensors available from Interlink Electronics. The resistive pressure sensors are formed in strips which can be cut to any desired length. The sensor strips are illustratively adhered to a stiffener and then sealed within a protective outer sleeve or cover made from a wipable material. Fasteners 116 are illustratively rivets which secure the sensors 114, 120, 122, and 124 in position on the deck 22 as best shown in FIG. 8. Sensors 114, 120, 122, and 124 are coupled to the controller 50 on the bed 10 by wires 126.

As pressure on the sensors 114, 120, 122, and 124 increases, resistance of the sensors is lowered. By processing the output signals from sensors 114, 120, 122, and 124, the controller 50 determines the position of the patient on the deck 22. In particular, the controller 50 determines when the patient moves away from a central portion of the bed and too close to the side edges 23 or 25 on the deck 22. Controller 50 then provides an indication that the patient is at risk of exiting the bed.

Using the two different types of sensors 70 and 104, the patient position detection apparatus of the present invention is capable of operating in several different modes to assist the caregiver with tracking the patient position on the bed 10. In an out-of-bed mode, only sensors 70 are used to activate an alarm when a patient completely exits the bed. In a second exiting mode, both sets of sensors 70, 104 are used. An alarm is activated when a patient is located at a position near the sides 23, 25 of deck 22 or on the deck 22 near the head end 26 or foot end 30. In other words, a pre-exit alarm is sounded when the patient moves outside a central portion of the deck 22 on the bed 10. In a third position mode, both sets of sensors 70, 104 are also used. An alarm is activated when a patient moves away from the head sensor 114 on the deck 22 as discussed below.

Figure 7:
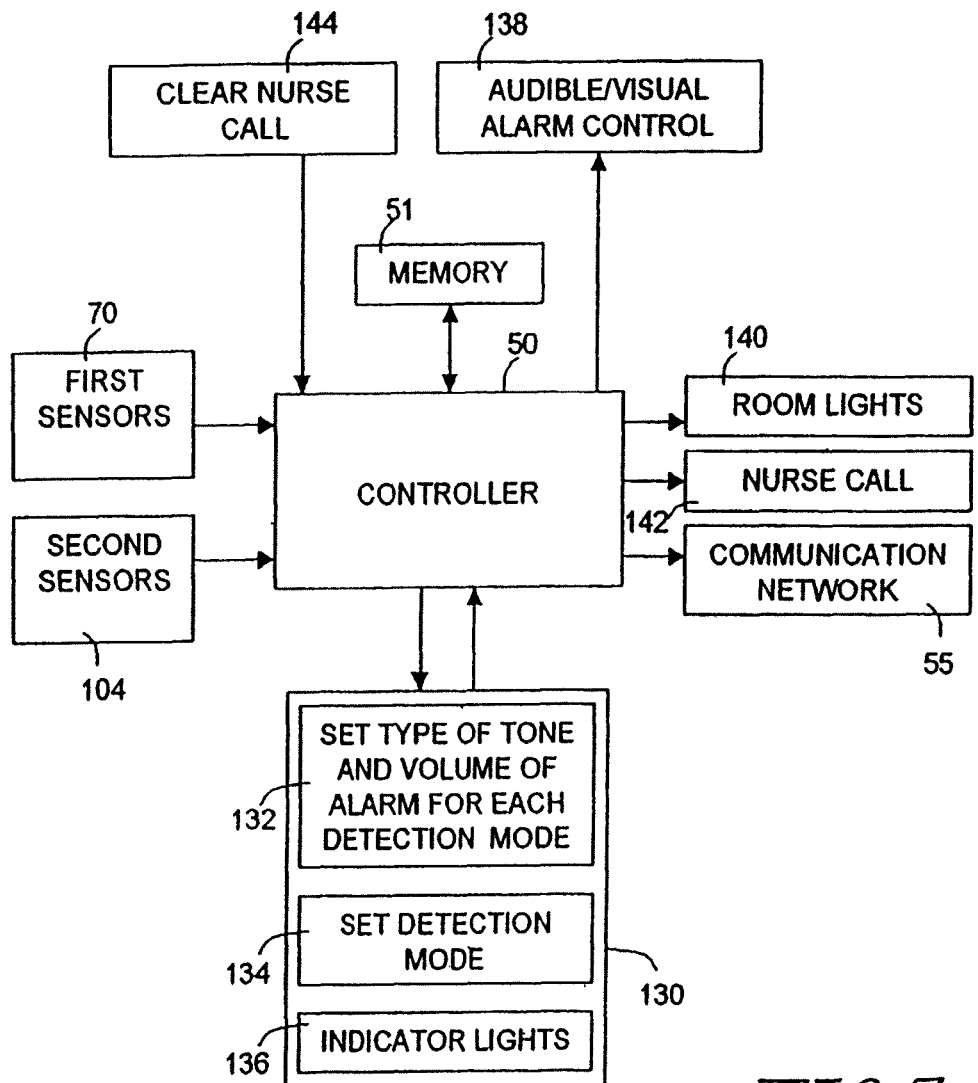
FIG. 7 is a block diagram illustrating the control electronics of the patient position detection apparatus.

FIG. 7 is a block diagram illustrating the electronic control components of the patient position detection apparatus. As discussed above, the first and second sensors 70 and 104 are each coupled to the controller 50. The controller 50 processes signals from the first and second sensors 70, 104 as discussed in detail below to provide various control functions. A caregiver control panel 130 is mounted on the bed 10 to control operation of the patient position detection apparatus. Preferably, the caregiver control panel 130 is mounted on the head end siderail 52 as best shown in FIG. 5. The control panel 130 may also be on a pendant or on a remote control device electrically coupled to the controller 50. The caregiver control panel 130 includes control buttons, switches, knobs, etc. for setting the particular type of tone for the audible alarm and for setting a volume of the alarm for each of the detection modes as illustrated at block 132. In addition, the caregiver control panel 130 includes control buttons, switches, knobs, etc. to set the particular type of detection mode for the apparatus as discussed below. Inputs from the caregiver control panel 130 are transmitted to the controller 50. Controller 50 also transmits signals to the caregiver control panel 130 to control indicator lights 136 on the caregiver control panel 130.

If an alarm condition is detected by controller 50 as discussed below in detail, controller 50 controls either audible or visual local alarms 138 within the room or on the bed 10. Controller 50 may also be used to turn on the room lights 140 when an alarm condition is detected. Finally, the controller 50 activates a nurse call alarm 142 to send an indication of the alarm condition to a nurse station located at a remote location.

The apparatus of the present invention further includes a nurse call reset or clear button 144 located on the bed 10. This clear button 144 sends a signal to controller 50 to clear the nurse call 142 alarm once the nurse call 142 alarm has been activated at the remote nurse call station. Nurse call clear button 144 permits the caregiver to clear or reset the remote patient alarm while at the bed 10 after responding to the alarm condition. Currently, caregivers must cancel the nurse call bed exit alarm 142 by returning to the nurse call station or by deactivating the alarm somewhere else in the hospital, other than at the bed 10. Button 144 permits the caregiver to clear the nurse call bed exit alarm 142 after responding to the alarm condition at the bed 10. Controller 50 is also coupled to a communication network 55 so that the controller 50 can transmit output signals to a remote location.

In an alternative embodiment of the present invention, controller 50 is programmed to deactivate the local alarm 138 if the patient returns to bed 10 or returns to a correct position on the bed 10 depending upon the mode selected. This feature may encourage the patient to return to the correct position on the bed 10 since the alarm will be deactivated when the patient returns to the correct position. The nurse call alarm 142 typically remains activated so that the caregiver may still respond to the alarm, even if the local audible and visual room alarm 138 is deactivated.

Figure 6:
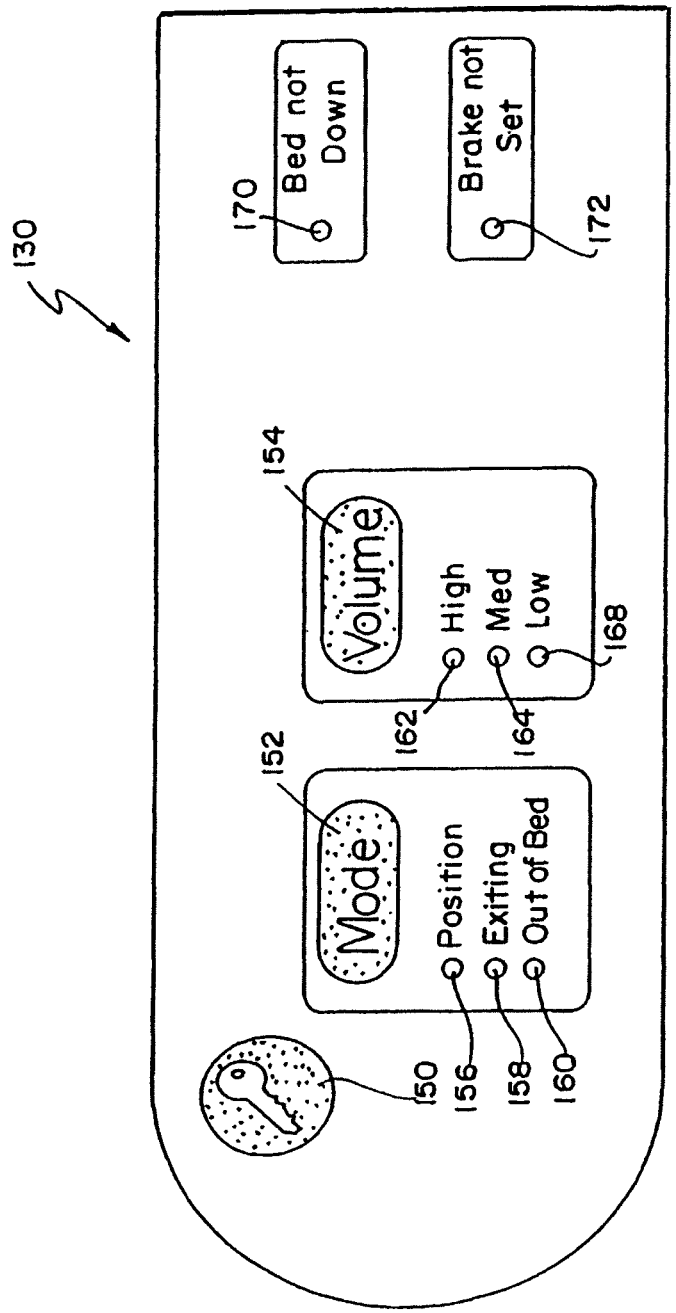
FIG. 6 is an enlarged view of the control panel of FIG. 5 which is used to control the mode of operation of the patient position detection apparatus and the volume of the alarms generated by the detection apparatus.

FIG. 6 illustrates further details of the caregiver control panel 130 which is illustratively located on the head end siderail 132. Control panel 130 includes a key button 150, a mode control button 152, and a volume control button 154. In order to adjust the detection mode or volume of the alarm, the caregiver must depress the key button 150 and hold it down while depressing the desired mode button 152 or volume button 154. With the key button 150 held down, the caregiver can scroll through the modes of operation by pressing the mode button 152. Separate indicator LEDs are provided to indicate which mode is selected. The Position Mode is indicated by LED 156, the Exiting Mode is indicated by LED 158, and the Out-of-Bed Mode is indicated by LED 160. If none of the LEDs 156, 158, 160 is lit, the patient position detection apparatus is off.

If the Position Mode is selected, all three LEDs 156, 158, and 160 are lit. If the Exiting Mode is selected, LEDs 158 and 160 are lit. If the Out-of-Bed Mode is selected, only LED 160 is lit. By providing a different number of indicator lights for each of the three modes, a caregiver can tell which mode is selected in the dark.

By requiring the depression of both the key button 150 and the mode button 152 or volume button 154 and by placing these buttons 150, 152, 154 on the caregiver side of the siderail 32, the patient is deterred from changing modes or volumes. The caregiver can change the volume of the alarm between a high setting, a medium setting, and a low setting by pressing the key button 150 and simultaneously pressing the volume button 154. Subsequent presses of the volume button 154 change the volume to different levels. Indicator LEDs 162, 164, and 166 are provided for the high, medium, and low volumes, respectively. If the high volume level is selected, all three LEDs 162, 164, and 168 are lit. If the medium volume level is selected, LEDs 164 and 168 are lit. If the low volume level is selected, only LED 168 is lit. By providing a different number of indicator lights for each volume level, a caregiver can tell the volume level for the alarm in the dark. When the patient position detection apparatus is off, all the volume LEDs 162, 164, and 168 are off.

When a local alarm condition is detected by controller 50 as discussed below. An appropriate LED for Position Mode, Exiting Mode, and Out-of-Bed Mode will flash on the control panel 30 to indicate an alarm condition for that mode. More than one of the LEDs 156, 158, and 160 can flash. For instance, in Position Mode, the Position Mode LED 156 may begin to flash when an alarm condition is detected by the Position Mode. Since the Out-of-Bed Mode is also run in Position Mode, the Out-of-Bed LED 160 may also be flashing if the patient has exited the bed.

Caregiver control panel 130 also includes an indicator LED 170 to provide an indication that the bed 10 is not down. This indicator LED 170 is lit when the deck 22 is not in its lowest position relative to the floor. In addition, caregiver panel 130 includes an indicator LED 172 which provides an indication when the brake on the casters 14 is not set. When positioned in a room, the bed 10 is typically set so that the deck 22 is in its lowest position and the brake is set. Therefore, indicator LEDs 170 and 172 provide the caregiver with an indication that these conditions are not met.

FIG. 8 shows the illustrative arrangement of the sensors 114, 120, 122, and 124 on the articulating deck 22. It is understood that other arrangements of the second set of sensors 104 may be used in accordance with the present invention. In addition, additional sensors may be provided such as a sensor 125 located on the leg deck section 112. Although the second sensors 104 are illustratively resistive sensors, it is understood that other types of sensors may be used in accordance with the present invention. For example, capacitance sensors such as shown in U.S. Pat. No. 5,808,552 or in U.S. patent application Ser. No. 09/031,749, now U.S. Pat. No. 6,067,019 which are incorporated herein by reference, may be used as the second sensors. In addition, a piezoelectric sensor such as disclosed in U.S. application Ser. No. 09/263,038, now U.S. Pat. No. 6,252,512, which is hereby incorporated by reference, may also be used. In another embodiment, the sensors 104 are coupled to a stop or bottom surface of the mattress 38 or are located within an interior region of the mattress 38.

Figure 9:
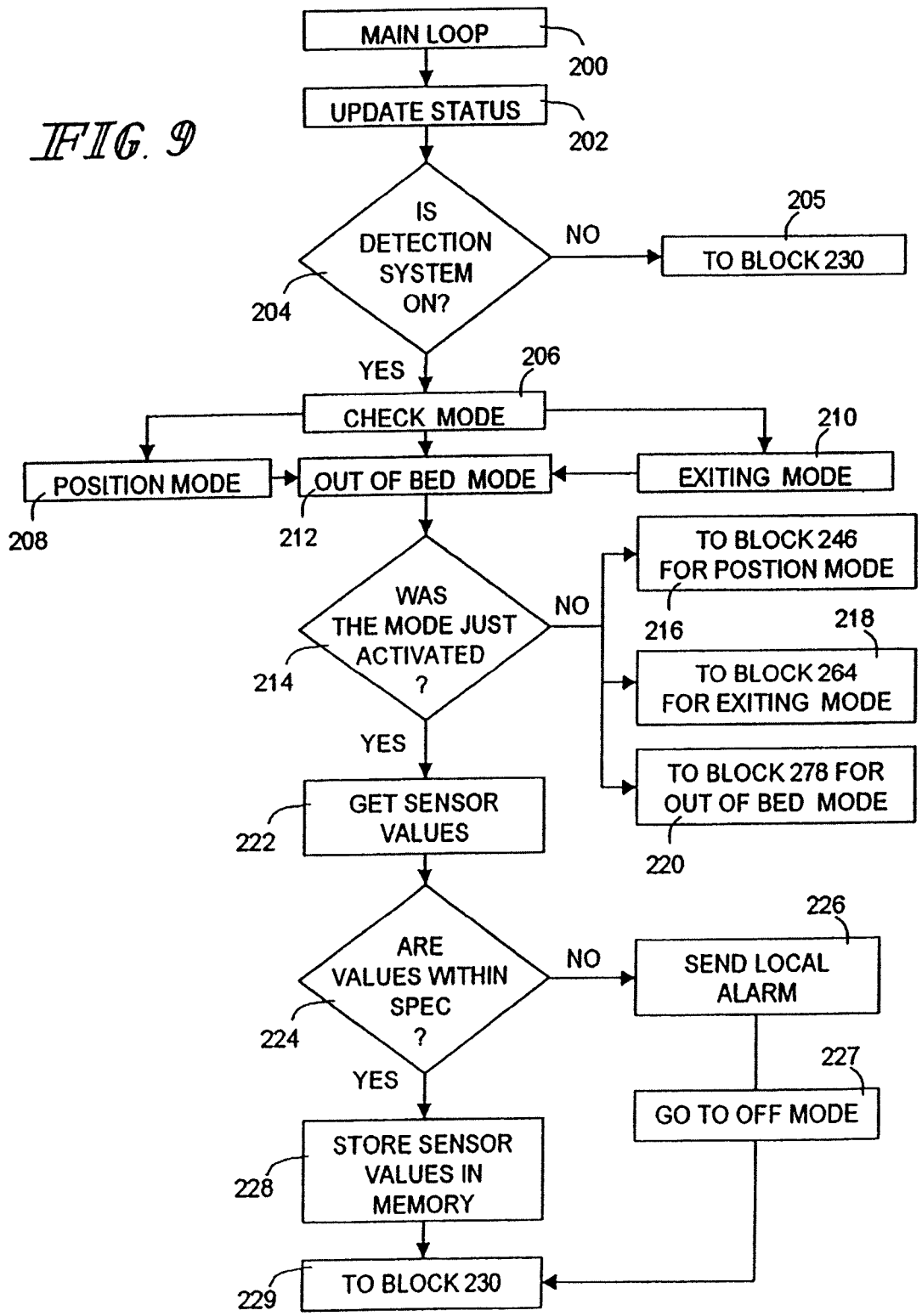
FIGS. 9 and 10 are flow charts illustrating a main loop of steps performed by the controller for monitoring inputs from the control panel and the first and second sets of sensors to control operation of the patient position detection apparatus in a position mode, an exiting mode, and an out-of-bed mode.
Figure 10:
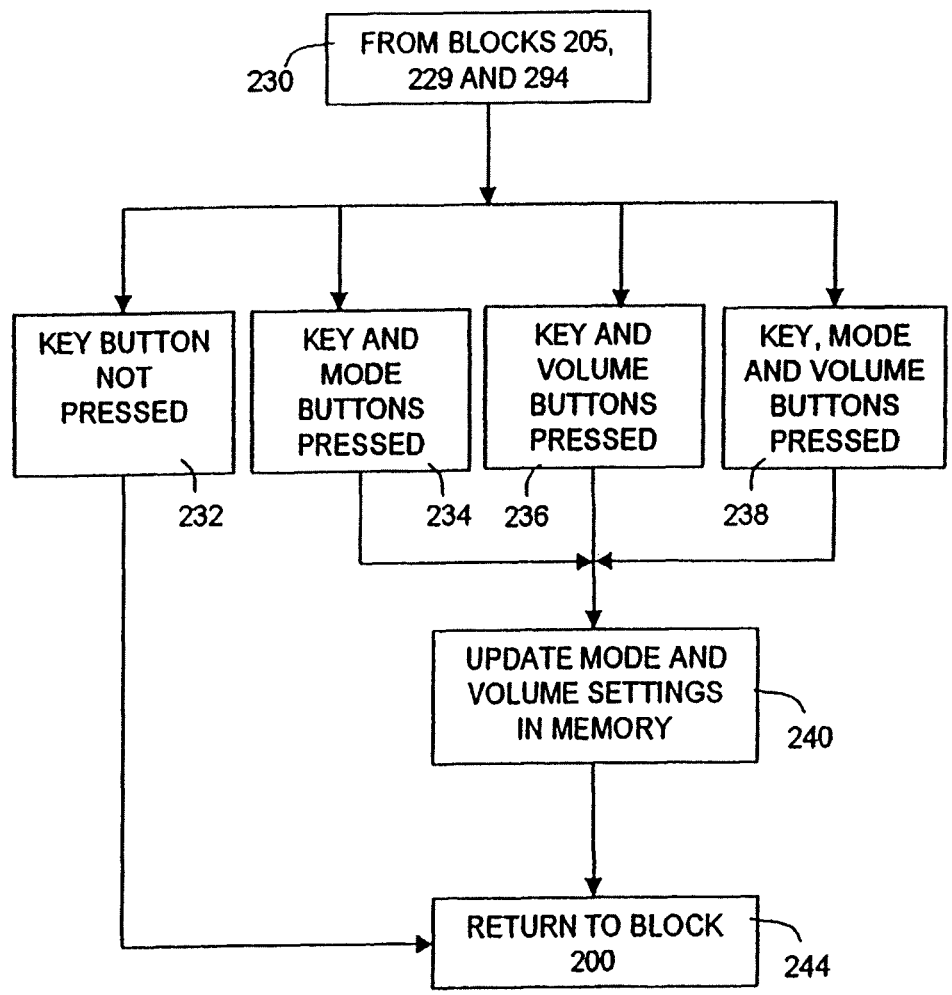

FIGS. 9-12 are flow charts illustrating operation of the controller 50 of the present invention and each of the three patient position detection modes. The main software loop of the controller 50 is illustrated in FIGS. 9 and 10. The main loop begins at block 200 of FIG. 9. Controller 50 first updates the status of the indicator lights 136 on control panel 130 or elsewhere as illustrated at block 202. Controller 50 then determines whether the patient detection system is on at block 204. If the detection system is not on, controller 50 advances to block 230 as illustrated at block 205. If the patient detection system is on, controller 50 checks the mode of the detection system as illustrated at block 206. Specifically, controller 50 determines whether the detection system is in position mode as illustrated at block 208, exiting mode as illustrated at block 210, or out-of-bed mode as illustrated at block 212.

If the controller is in position mode as illustrated at block 208 or exiting mode as illustrated at block 210, the controller 50 will run the control loops for these modes as discussed below. After running the positioning mode loop or the exiting mode loop, the controller 50 will also run the out-of-bed mode loop when the controller is set in position mode or exiting mode. In other words, if the detection system is on, the out-of-bed mode will always be checked.

Controller 50 then determines whether the mode was just activated at block 214. If the particular mode was not just activated, the controller 50 advances to block 246 of FIG. 11 if the system is in position mode as illustrated at block 216. If the particular mode was not just activated, controller 50 advances to block 264 of FIG. 12 if the system is in exiting mode as illustrated at block 218. If the particular mode was not just activated, controller 50 advances to block 278 of FIG. 13 if the system is in out-of-bed mode as illustrated at block 220.

If the mode was just activated at block 214, controller 50 reads all the sensor values from the first and second sets of sensors 70 and 104 as illustrated at block 222. Controller 50 then determines whether the sensor values are within the preset specifications as illustrated at block 224. In the position mode, controller 50 is only concerned with the head sensor 114. Therefore, in position mode, the output from head sensor 114 is checked. The output value from sensor 114 is within specification if the head sensor 114 output signal corresponds to a range of weights between 50-450 lbs. Therefore, for position mode, the sensor 114 is typically not within specification if the head sensor 114 is not plugged in, shorted, or if a patient is not on the bed 10.

For exiting mode, controller 50 checks all the load cells 70 and sensors 114, 120, 122, and 124. To be within specification for exiting mode, the weight range detected by load cells 70 must be within a predetermined range based on average human weights. Controller 50 also determines whether any of the sensors 114, 120, 122, or 124 are not plugged in or are shorted. In the out-of-bed mode, controller 50 only looks at load cells 70 to make sure that at least a predetermined minimum weight reading is obtained in order to indicate that a patient is on the bed 10.

If the values read at block 222 are not within specifications, controller 50 will send a local alarm as illustrated at block 226 so that the caregiver can investigate the problem as illustrated at block 226. Controller 50 then turns the detection system off as illustrated at block 227 and advances to block 230 as illustrated at block 229. If the retrieved sensor values are within the specifications at block 224, controller 50 stores all the sensor values in memory 51 as illustrated at block 228. Controller 50 then advances to block 230 as illustrated at block 229.

In the illustrated embodiment, the key button 150 on control panel 130 is a hardware switch. If the key button 50 is not pressed, the controller 50 does not receive the signal from the mode button 152 or the volume button 154. Therefore, if the key button is not pressed as illustrated at block 232, controller 50 returns to block 200 as illustrated at block 244. If the key button 150 and the mode button 152 are pressed as illustrated at block 234, the controller 50 will receive an input based on the mode button press. If the key button 150 and the volume button 154 are pressed as illustrated at block 236, the controller 50 will receive an input signal from the volume button 154 press. If the key button 150, the mode button 152, and the volume button 154 are all pressed as illustrated at block 238, the controller 50 will receive input signals from both the mode button press and the volume button press. If the key button and at least one other button are pressed at blocks 234, 236, and 238, controller 50 will update the mode and volume settings in memory 51 as illustrated at block 240. Controller 50 then returns to block 200 as illustrated at block 244.

Figure 11:
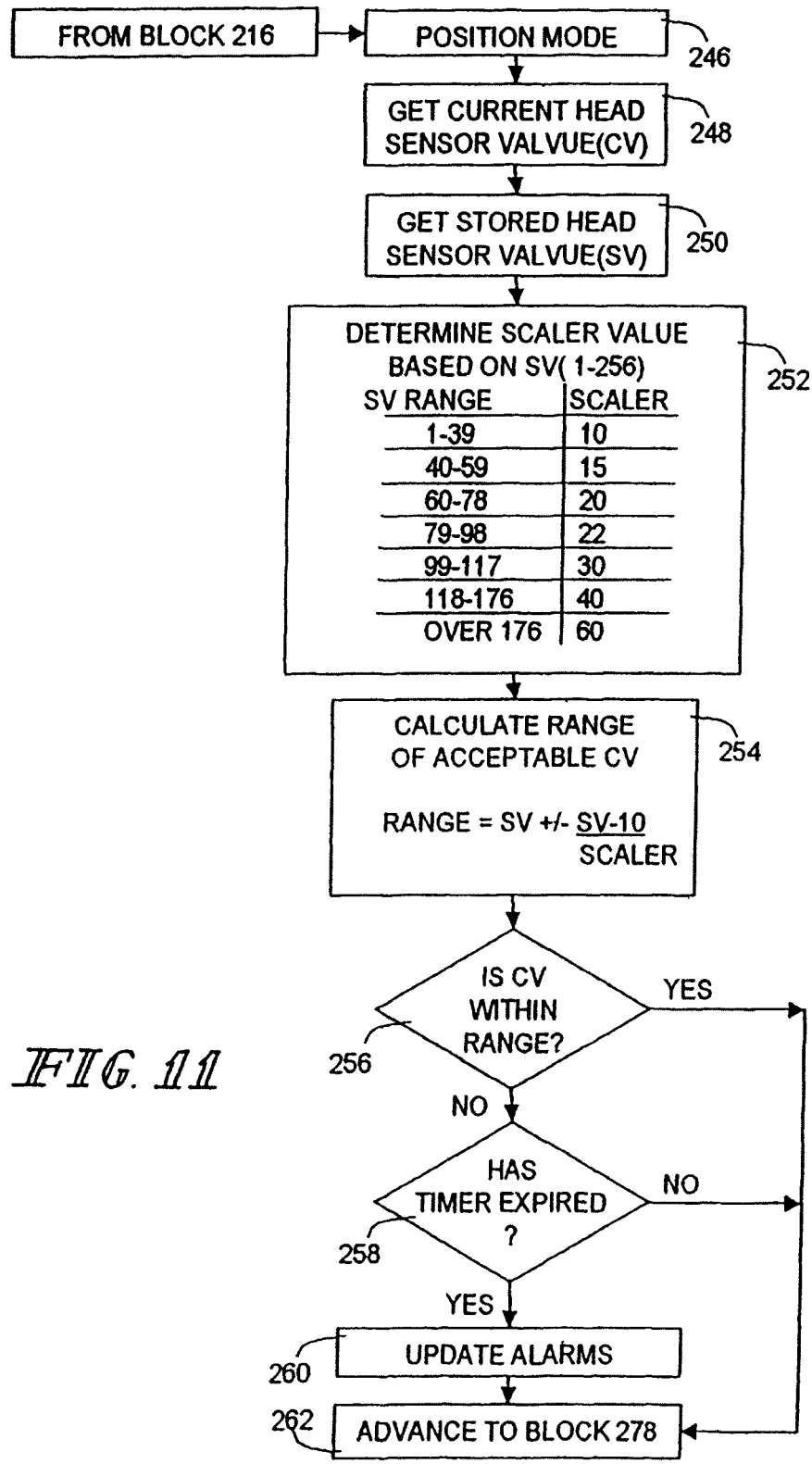
FIG. 11 is a flow chart illustrating steps performed by the controller in the position mode.

Operation of the controller 50 in position mode is illustrated beginning at block 246 of FIG. 11. Controller 50 first reads the current value of head sensor 114 as illustrated at block 248. The current head sensor value is abbreviated as CV. Next, controller 50 retrieves the stored value for head sensor 114 which was stored in memory 51 at block 228 as illustrated at block 250. The stored sensor value is abbreviated as SV. Controller 50 then determines a scaler value based upon the stored head sensor value. In the illustrated embodiment, an 8 bit A/D converter is used to convert the output from the sensors 104. Therefore, the value SV ranges from 1-256 in the illustrated embodiment. Smaller values of SV indicate larger weight on the sensors 104. It is understood that this range could be varied depending upon the particular A/D converter used. Therefore, the range of 1-256 is only for illustrative purposes. Controller 50 sets the scaler value as illustrated in the table at block 252. The scaler value remains constant until the mode is reactivated. Next, controller 50 calculates the acceptable range for the current head sensor value (CV) as illustrated at block 254. The acceptable range is:

Controller 50 determines whether the current head sensor value CV is within the acceptable range as illustrated at block 256. If so, controller 50 determines that the patient is in the proper position on the deck and returns to block 230 as illustrated at block 262. If the current head sensor value is not within the acceptable range at block 256, controller 50 determines whether a timer has expired at block 258. If not, controller 50 advances back to block 230. If the timer has expired, controller 50 determines that the patient is out of position and activates the local alarms 138 as illustrated at block 260. Controller 50 also activates a nurse call alarm 142, and may turn on the room lights 140 at block 260. Controller 50 then advances to block 278 and runs the out-of-bed mode check as illustrated at block 262.

Figure 12:
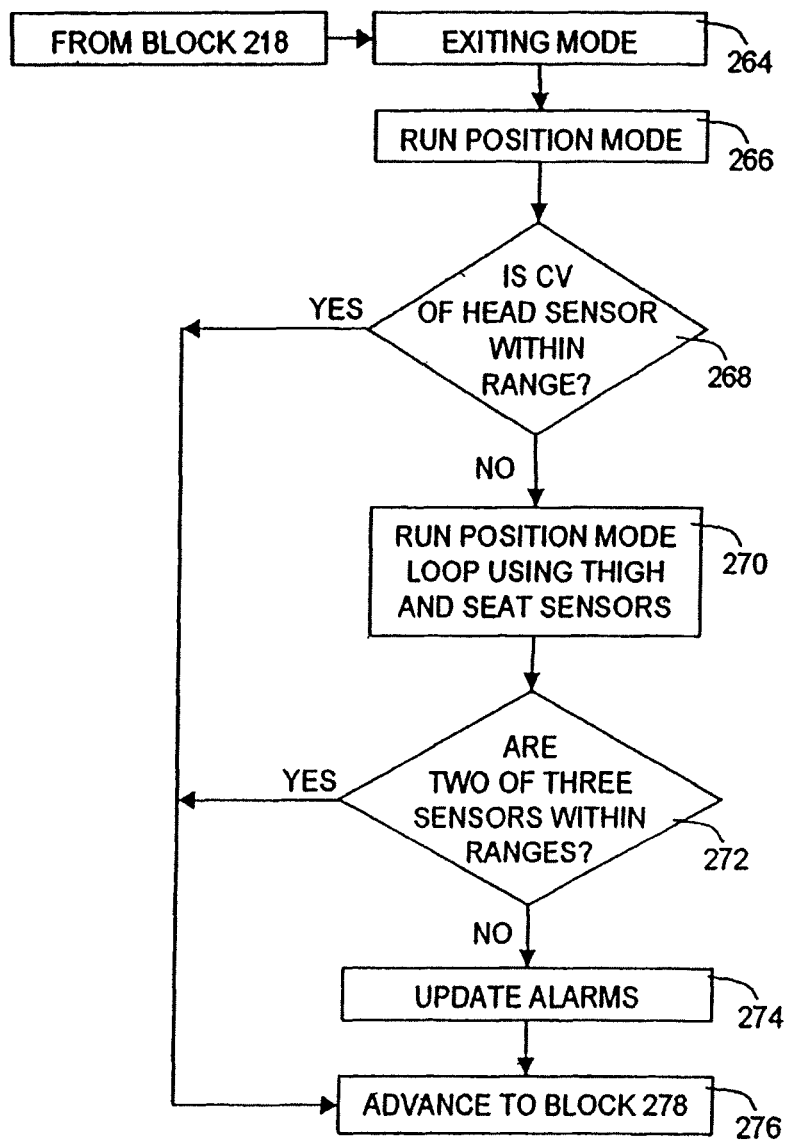
FIG. 12 is a flow chart illustrating steps performed by the controller in the exiting mode.

Operation of the patient detection system in exiting mode is illustrated beginning at block 264 in FIG. 12. Controller 50 advances to block 264 from block 218 in FIG. 9. In exiting mode, controller 50 first runs the positioning mode loop as illustrated at block 266. In other words, the controller 50 uses head sensor 114 to check the patient's position using the flow chart discussed above in reference to FIG. 11. Controller 50 determines whether the current head sensor value CV is within the acceptable range as illustrated at block 268. If so, controller 50 determines that the patient is in the proper position and advances to block 278 to run the out-of-bed mode check as illustrated at block 276 in FIG. 12.

If the head sensor value is not within the acceptable range at block 268, controller 50 runs a sensor test for seat sensor 120 and thigh sensors 122 and 124 using a similar test as in FIG. 11. Scaler values may be adjusted for the different sensors 120, 122, and 124, if necessary. Scaler values are selected by applying a known load above a particular sensor location and taking an output reading. Next, a predetermined distance from the sensor is selected at which point it is desired to activate the alarm. The known weight is than moved to that desired alarm location and another output reading is taken. The scaler value is calculated the percentage change between the output of the sensor when the known weight applied directly over the sensor and the output of the sensor when the known weight applied at the predetermined distance perpendicular to the sensor.

Controller 50 then determines whether two of the three remaining sensors 120, 122, and 124 are within acceptable ranges as illustrated at block 272 by comparing the current sensor values to ranges based on the corresponding stored sensory values. If so, controller 50 determines that the patient is in an acceptable position on the deck 22 and advances at block 230 as illustrated at block 276. If two of the three sensors are not within the acceptable ranges at block 272, controller 50 determines that the patient is out of position and updates the local alarms 238, activates the nurse call alarm 142, and may turn on the room lights 140 as illustrated at block 274. Controller 50 then advances to block 230 as illustrated at block 276. In exiting mode, the patient position detection apparatus of the present invention permits the patient to move around more on the deck 22 before an alarm is activated compared to the position mode. Therefore, position mode is the most sensitive setting for the patient position detection apparatus of the present invention.

It is understood that other configurations may be provided for the locations of sensors 104. A different number of sensors 104 may be used. The sensors 104 may be mounted at different locations on the deck 22, on the mattress 38, or elsewhere on the bed 10.

Figure 13:
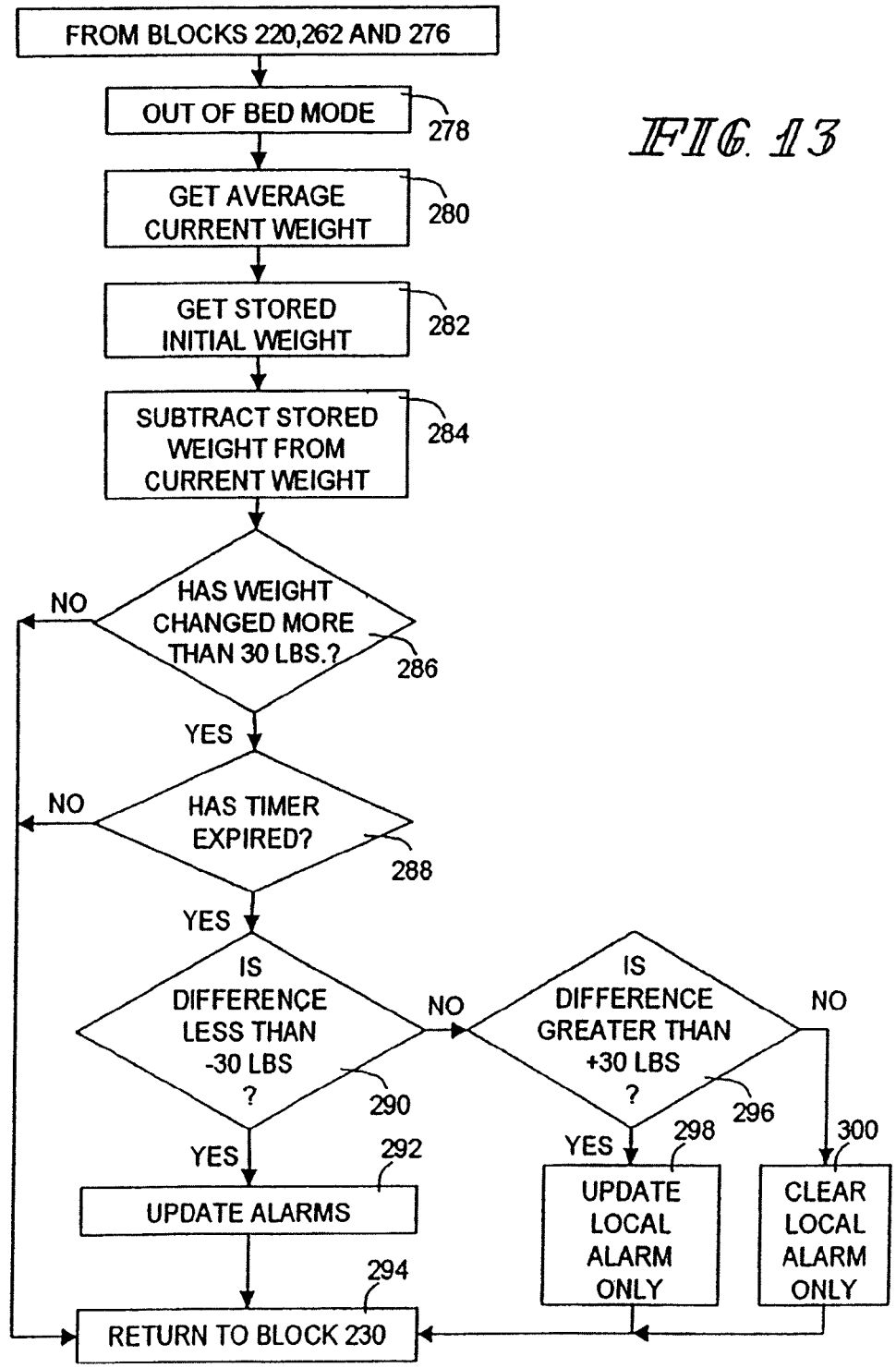
FIG. 13 is a flow chart illustrating steps performed by the controller in the out-of-bed mode.

Operation of the patient position detection system in the out-of-bed mode is illustrated beginning at block 278 in FIG. 13. Controller 50 advances to block 278 from block 220 in FIG. 9. In the out-of-bed mode, controller 50 detects an average current weight of the patient as illustrated at block 280. For instance, the controller 50 can take four readings from each load cell 70 and divide by four to get an average current weight. Next, controller 50 retrieves the stored initial weight from memory 51 as illustrated at block 282. Controller 50 subtracts the stored weight from the current weight as illustrated at block 284.

Next, controller 286 determines whether the weight on the bed 10 detected at block 280 has increased or decreased by more than 30 lbs. compared to the initial stored weight retrieved at block 282. If the weight has not changed by more than 30 lbs., controller returns to block 230 as illustrated at block 294. If the weight has changed by more than 30 lbs. at block 286, controller 50 determines whether a timer has expired at block 288. If the timer has not expired, controller 250 advances to block 230 as illustrated at block 294. If the timer has expired at block 288, the controller 50 determines whether the difference calculated at block 284 is less than −30 lbs. at block 290. If so, controller 50 determines that the patient has exited the bed 10 and updates the local alarms 138, the nurse call alarm 142 and may turn on the room lights 140 as illustrated at block 292. Controller 50 then returns to block 230 as illustrated at block 294.

If the difference is not less than −30 lbs. at block 290, controller 50 determines whether the difference calculated at block 284 is greater than 30 lbs. as illustrated at block 296. If so, controller 50 determines that substantial additional weight has been added to the bed and updates local alarms 138 only as illustrated at block 298. The nurse call alarm 142 may also be activated, if desired. Controller 50 then advances to block 230 as illustrated at block 294. If the difference is not greater than 30 lbs. at block 296, controller 50 clears the local alarm only at block 300 and then advances to block 230 as illustrated at block 294.

It is understood that the 30 lbs. threshold value for the out-of-bed mode may be adjusted upwardly or downwardly depending upon the weight of the patient. In other words, if the patient is particularly heavy, the 30 lb. threshold may be increased, for example.

It is understood that the patient detection apparatus of the present invention may have more than three modes of operation if desired. The separate modes may have different sensitivity levels.

The out-of-bed mode of the present invention may be armed with the patient in the bed 10. In some beds having scales, the patient must be removed in order to determine a tare weight of the bed prior to the patient getting into the bed in order to arm the bed exit detector. In the out-of-bed mode of the present invention, removing the patient from the bed is not required in order to arm the bed exit detection system.

The patient position detection system of the present invention may be quickly switched from a normal bed exit system in which an alarm is generated only when a patient exits the bed to a predictive bed exit system in which an alarm is generated when a patient moves away from a center portion of the bed. In an embodiment of the invention, the output signals from the first and second set of sensors 70, 104 are monitored and stored, either at the bed 10, or at a remote location to record movements of the patient. The controller 50 or a controller at the remote location monitors the sensor output values to determine whether the patient is moving on the bed 10. In one embodiment, the controller 50 or controller at a remote location generates a caregiver alert signal or alarm if the patient has not moved on the bed within a predetermined period of time. Therefore, the caregiver can go to the bed 10 and rotate the patient in order to reduce the likelihood that the patient will get bed sores. For example, if the patient hasn't moved for a predetermined period of time, such as two hours, a signal is generated advising the caregiver to move the patient. If the sensors 70, 104 and controller detect that the patient has moved within the predetermined period, then there is no need for the caregiver to go turn the patient. Therefore, no signal is generated. This feature saves caregiver time and reduces the likelihood of injuries due to unnecessary rotation of a patient who has been moving.

In another embodiment of the present invention, the output signals from the four sensors 70 located at the corners of the base frame 12 are used to provide an indication when one of the frames or the deck hits an obstruction when moving from the high position to a low position. In particular, the processor 50 determines when an output signal from one of the sensors 70 at the corners generates a negative value or a greatly reduced weight reading within a short period of time. This rapid change in the output signal indicates that an obstruction has been hit. Therefore, controller 50 can provide an output signal to stop the hi/lo mechanism from lowering the frames and deck. An alarm signal is also provided, if desired.

In another embodiment of the present invention, the controller 50 is configured to transmit data to a nurse station located at a remote location over the communication network 55. This data illustratively includes information related to at least one of patient weight, the patient's position on the support surface of the bed 10, a bed exit indicator, the mode of operation of the patient position detection apparatus, a brake not set indicator, a bed not down indicator, or other data related to the status of the bed or the status of the patient. This permits the nurse to detect the information related to the status of the bed or the status of the patient at the central nurse station without having to check each bed separately.

Figure 16:
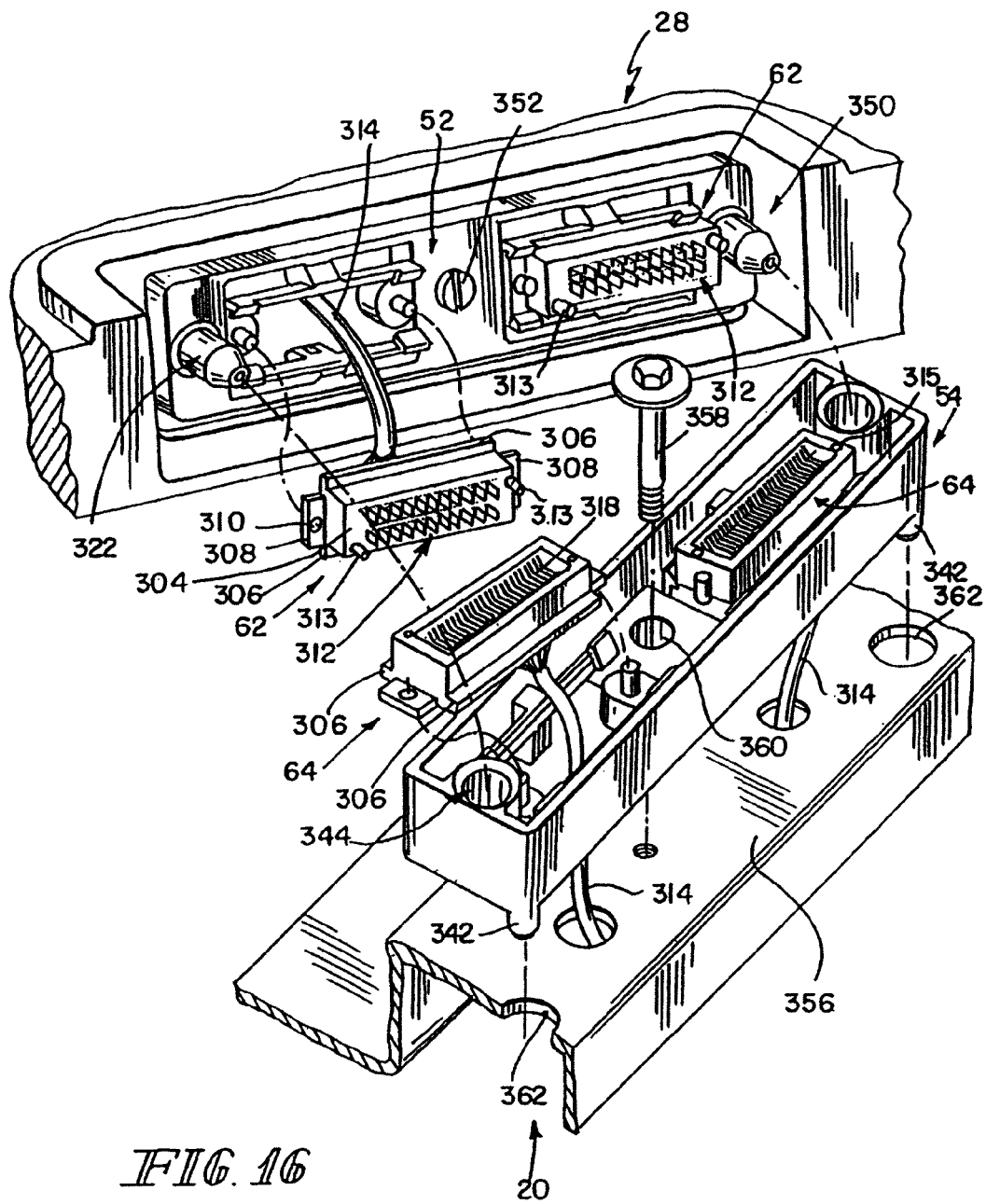
FIG. 16 is an exploded perspective view illustrating the first and second electrical connector apparatuses with electrical connectors installed therein and located on the footboard and retracting frame, respectively.

FIGS. 14-16 further illustrate the connector alignment apparatus of the present invention. The first connector alignment apparatus 52 is illustrated in FIG. 14, and the second connector alignment apparatus 54 is illustrated in FIG. 15. Connector alignment apparatus 52 is configured to receive a first pair of electrical connectors 62 shown in FIG. 16 which include a housing 304 having a first pair of spaced-apart flanges 306 and a second pair of spaced-apart flanges 308. Flanges 308 are each formed to include an aperture 310. Connectors 302 include a plurality of electrical terminals 312 extending away from housing 304. Alignment posts 313 extend from housing 304 of connector 62 further than terminals 312. The terminals 312 are electrically connected to conductors of a cable 314. Cable 314 of connectors 62 are connected to controls 40. Connector alignment apparatus 54 is configured to receive female electrical connectors 64. Those numbers referenced by numbers on connectors 62 perform the same or similar function. Connectors 64 include female socket contacts 318 configured to receive terminals 312 of connector 302. Illustratively, cables extending from connectors 64 are coupled to the controller 50 on bed 10.

Referring now to FIG. 14, connector alignment apparatus 52 includes a base plate 320 having outwardly extending alignment posts 322 located at opposite ends. Posts 322 each include tapered head portions 324. Alignment apparatus 52 includes a pair of connector receiving portions 326. Connector receiving portions 326 each include a pair of center posts 328. Each post 328 includes a pair of spring arms 330. Each spring arm 330 has a head portion 332 including a ramp surface 334 and a bottom lip 336. Each connector receiving portion 326 also includes a pair of posts 338.

Electrical connectors 62 are installed into the connector receiving portions 326 by locating the apertures 310 on flanges 308 over the posts 338 and pushing the connector 62 toward base 320. Flanges 306 engage ramp surfaces 334 of heads 332 and cause the spring arms 330 to be deflected. Once the flanges 306 move past the heads 332, heads 332 then move over flanges 306 to retain the connectors 302 within the connector alignment apparatus 52 as best shown in FIG. 16.

Second connector alignment apparatus 54 is best illustrated in FIG. 15. The alignment apparatus includes a body portion 340 having a pair of downwardly extending alignment posts 342. Body portion 340 is formed to include apertures 344 at opposite ends. Apertures 344 are configured to receive the posts 322 of first connector alignment apparatus 52 as discussed below. Lead-in ramp surfaces 346 are formed around the apertures 344. Body portion 340 further includes a pair of connector receiving portions 348 which function the same as connector receiving portions 326 described above. Reference numbers the same as in FIG. 14 perform the same or similar function. Apertures 310 formed in flanges 308 of connectors 64 are inserted over the posts 338 of the connector receiving portions 348. The connectors 64 are then pushed downwardly to deflect the heads 332 until the lips 336 move over flanges 306 to lock the connectors 64 within the housing 340 as discussed above.

The first connector alignment apparatus 52 and the second connector alignment apparatus 54 each may include a key shown diagrammatically at locations 349 and 351, respectively. Certain beds have different features which are controlled by controller 50 and actuated by controls 40 on the footboard. Therefore, different footboards 28 may be required depending upon the particular type of bed 10 being used. The keys 349 and 351 on the first and second connector alignment apparatuses 52 and 54 only permit connection between an appropriate type of footboard 28 for the particular bed 10. Therefore, the keys 349 and 351 ensure that the right type of footboard 28 is attached to the bed 10.

First connector alignment apparatus 52 is rigidly coupled within a recessed portion 350 formed in footboard 28 as best shown in FIG. 16. The base 320 is secured to the footboard 28 by a fastener 352 which extends through an aperture 354 formed in the base 320. The second connector alignment apparatus 54 is loosely connected to an end surface 356 of the frame 20. A fastener 358 is configured to extend through an oversized central opening 360 formed in housing 340. Posts 342 at opposite ends of the housing 340 are located within apertures 362 formed in the surface 356 of the frame 20. Housing 340 is therefore not rigidly coupled to frame 20 and can float slightly due to the oversized apertures 362 and the oversized aperture 360.

During installation of the footboard 28 on to the frame 20, initial alignment is provided by posts 58 on frame 20 extending into the apertures 56 formed in the footboard 28. As the footboard 28 moves downwardly over the posts 58, the posts 322 on first connector alignment apparatus 52 enter the apertures 344 in the second connector alignment apparatus 54. Tapered surfaces 324 on posts 22 and tapered surfaces 346 of apertures 344 facilitate insertion of the posts 322 into the apertures 344. Since the housing 340 of second connector alignment apparatus 54 can float on the frame 20, the housing 340 moves into proper alignment with the first connector alignment apparatus 52 as the footboard 28 is installed. This ensures proper alignment between connectors 62 and 64. Typically, connectors 62 and 64 include further alignment posts 313 and apertures 315, respectively, which mate to make sure that each of the terminals 312 line up with the socket contacts 318. Therefore, the connector alignment apparatus of the present invention includes a combination of posts 58 on the frame 20 which mate with aperture 56 on the footboard 28, posts 322 on the first connector alignment apparatus 52 which mate with apertures 344 on the second connector alignment apparatus 54, and posts 313 on connectors 62 which mate with apertures 315 on the connectors 64 to provide further alignment.

Although the invention has been described in detail with reference to certain illustrated embodiments, variations and modifications exist within the scope and spirit of the invention as described and as defined in the following claims.

The invention claimed is:

1. A bed comprising:
a frame including a lower frame and an upper frame movable between a raised position and a lowered position relative to the lower frame,
a plurality of casters coupled to the lower frame,
a braking system operable to brake and unbrake the casters,
a controller coupled to the frame,
a patient position detection system which has multiple modes of operation from which to select for determining a location of a patient relative to the frame, each mode of the multiple modes of operation having a different sensitivity so that a different amount of patient movement is required before an alarm condition is considered to exist, and
at least one alert light coupled to the controller, wherein the frame includes a plurality of barriers including a plurality of siderails, a headboard and a footboard, wherein the at least one alert light is coupled to one of the barriers, wherein the controller operates to change a state of the at least one alert light in response to at least one of the upper frame not being in the lowered position and the casters not being braked.

2. The bed of claim 1, wherein the barrier to which the at least one alert light is coupled also carries at least one user input of the patient position detection system.

3. The bed of claim 2, wherein the at least one user input of the patient position detection system is usable to select which of the multiple modes of operation the patient position detection system operates.

4. The bed of claim 2, wherein the at least one user input of the patient position detection system is usable to select a volume at which an audible alarm of the patient position detection sounds when the alarm condition associated with a selected one of the multiple modes of operation is detected.

5. The bed of claim 1, wherein the alert light is coupled to at least one of the siderails of the plurality of siderails.

6. The bed of claim 1, wherein the footboard has user inputs that are usable to provide commands to the controller.

7. The bed of claim 6, wherein the footboard is decouplable from the remainder of the frame and the user inputs are decoupled from the controller when the footboard is decoupled from the remainder of the frame.

8. The bed of claim 1, wherein the patient position detection system includes a plurality of sensors and signals from the plurality of sensors are used to determine whether to activate an alarm based on the signals and a selected mode of operation.

9. The bed of claim 8, wherein a weight of a patient supported by the frame is determined based on signals generated by the plurality of sensors.

10. The bed of claim 9, further comprising a display coupled to the footboard, the display being operable to display the weight of the patient.

11. The bed of claim 1, wherein the controller is configured to send a signal that results in activation of at least one light spaced from the bed in response to the alarm condition being detected.

12. The bed of claim 1, wherein at least one of the barriers is a detachable barrier that is decoupleable from the remainder of the frame and the alert light remains with the frame when the detachable barrier is decoupled from the remainder of the frame.

13. The bed of claim 12, wherein the detachable barrier comprises at least one of the headboard and the footboard.

14. A bed comprising:
a frame including a lower frame and an upper frame movable between a raised position and a lowered position relative to the lower frame,
a plurality of casters coupled to the lower frame,
a braking system operable to brake and unbrake the casters,
a controller coupled to the frame,
a patient position detection system which has multiple modes of operation from which to select for determining a location of a patient relative to the frame, each mode of the multiple modes of operation having a different sensitivity so that a different amount of patient movement is required before an alarm condition is considered to exist, and
at least one alert light coupled to the controller, wherein the frame includes a plurality of barriers including a plurality of siderails, a headboard and a footboard, wherein the at least one alert light is coupled to one of the barriers, wherein the multiple modes of operation includes first, second, and third modes, the first mode of operation resulting in the alarm condition being considered to exist in the event the first mode is the selected mode and the patient moves by a first amount, the second mode of operation resulting in the alarm condition being considered to exist in the event the second mode is the selected mode and the patient moves by a second amount greater than the first amount, and the third mode of operation resulting in the alarm condition being considered to exist in the event the third mode is the selected mode and the patient moves a third amount greater than the second amount.

15. The bed of claim 14, wherein the third mode of operation results in the alarm condition being considered to exist in the event the patient exits the frame.

16. The bed of claim 14, wherein the patient position detection system includes first, second, and third mode indicator lights which correspond to the first, second, and third modes of operation of the patient position detection system, respectively, and the indicator lights indicating which mode of the first, second, and third modes has been selected.

17. A bed comprising:
a frame including a lower frame and an upper frame movable between a raised position and a lowered position relative to the lower frame,
a plurality of casters coupled to the lower frame,
a braking system operable to brake and unbrake the casters,
a controller coupled to the frame,
a patient position detection system which has multiple modes of operation from which to select for determining a location of a patient relative to the frame, each mode of the multiple modes of operation having a different sensitivity so that a different amount of patient movement is required before an alarm condition is considered to exist, and
at least one alert light coupled to the controller, wherein the frame includes a plurality of barriers including a plurality of siderails, a headboard and a footboard, wherein the at least one alert light is coupled to one of the barriers, wherein the at least one alert light comprises a first alert light to indicate whether the upper frame is not lowered and a second alert light to indicate that the casters are not braked.

18. The bed of claim 17, further comprising at least one third light to indicate the selected mode of the multiple modes of the patient position detection system.

19. The bed of claim 18, further comprising at least one fourth light to indicate a volume at which an audible alarm of the patient position detection system is to sound in the event of the alarm condition of the selected mode of operation being detected.

* * * * *